US011800917B2

(12) United States Patent
Ferebee Maher et al.

(10) Patent No.: US 11,800,917 B2
(45) Date of Patent: Oct. 31, 2023

(54) HAIR-TREATMENT COMPOSITIONS AND METHODS OF USE

(71) Applicant: L'OREAL, Paris (FR)

(72) Inventors: Rachel Ferebee Maher, Morristown, NJ (US); Ronak Rughani, Edison, NJ (US); Halil Gevgilili, Weehawken, NJ (US)

(73) Assignee: L'OREAL, Paris (FR)

( * ) Notice: Subject to any disclaimer, the term of this patent is extended or adjusted under 35 U.S.C. 154(b) by 513 days.

(21) Appl. No.: 16/117,549

(22) Filed: Aug. 30, 2018

(65) Prior Publication Data

US 2020/0069025 A1 Mar. 5, 2020

(51) Int. Cl.
| | |
|---|---|
| *A45D 19/16* | (2006.01) |
| *A61K 8/06* | (2006.01) |
| *A61K 8/60* | (2006.01) |
| *A61K 8/73* | (2006.01) |
| *A61K 8/898* | (2006.01) |
| *A61K 8/92* | (2006.01) |
| *A61Q 5/00* | (2006.01) |
| *A61Q 5/12* | (2006.01) |
| *A45D 19/00* | (2006.01) |

(52) U.S. Cl.
CPC .............. *A45D 19/16* (2013.01); *A61K 8/062* (2013.01); *A61K 8/60* (2013.01); *A61K 8/73* (2013.01); *A61K 8/736* (2013.01); *A61K 8/898* (2013.01); *A61K 8/922* (2013.01); *A61Q 5/002* (2013.01); *A61Q 5/12* (2013.01); *A45D 19/0041* (2021.01); *A45D 2200/15* (2013.01); *A61K 2800/30* (2013.01); *A61K 2800/592* (2013.01)

(58) Field of Classification Search
None
See application file for complete search history.

(56) References Cited

U.S. PATENT DOCUMENTS

| | | | |
|---|---|---|---|
| 4,542,014 A | | 9/1985 | Bresak et al. |
| 4,786,494 A | * | 11/1988 | Hirota ................ A61K 8/60 424/59 |
| 5,141,964 A | * | 8/1992 | Noel ................ A61Q 19/00 514/777 |
| 5,554,313 A | * | 9/1996 | Chandler ............. A61K 8/4973 424/70.12 |
| 6,486,105 B1 | | 11/2002 | Cannell et al. |
| 6,635,240 B1 | | 10/2003 | Bolich et al. |
| 6,800,302 B2 | | 10/2004 | Cannell et al. |
| 7,204,861 B2 | | 4/2007 | Marsh et al. |
| 7,459,150 B2 | | 12/2008 | Cannell et al. |
| 7,601,212 B2 | | 10/2009 | Sabesan et al. |
| 8,652,456 B2 | | 2/2014 | Pierobon et al. |
| 8,795,643 B1 | | 8/2014 | Anthony |
| 2004/0166126 A1 | | 8/2004 | Cannell et al. |
| 2004/0241114 A1 | | 12/2004 | Gupta |
| 2009/0068136 A1 | * | 3/2009 | Beumer ................ A61K 8/463 424/70.16 |
| 2009/0074875 A1 | | 3/2009 | Wertz et al. |
| 2010/0215604 A1 | * | 8/2010 | Van Flodrop .......... A61K 8/898 424/70.2 |
| 2011/0236493 A1 | | 9/2011 | Canham et al. |
| 2011/0274731 A1 | * | 11/2011 | Miyahara ............... A61K 8/342 424/400 |
| 2012/0204894 A1 | * | 8/2012 | Odoms ................ A61K 8/678 132/202 |
| 2013/0224123 A1 | | 8/2013 | Wertz et al. |
| 2013/0319449 A1 | | 12/2013 | Xavier et al. |
| 2014/0090660 A1 | | 4/2014 | Xavier et al. |
| 2014/0116457 A1 | | 5/2014 | Krueger |
| 2014/0120047 A1 | | 5/2014 | Krueger |
| 2014/0120048 A1 | | 5/2014 | Krueger |
| 2014/0234225 A1 | | 8/2014 | Wertz et al. |
| 2015/0297496 A1 | | 10/2015 | Kroon et al. |
| 2016/0067163 A1 | | 3/2016 | Meyer et al. |
| 2016/0128944 A1 | | 5/2016 | Chawrai et al. |

FOREIGN PATENT DOCUMENTS

| | | |
|---|---|---|
| CN | 108324591 A | 7/2018 |
| DE | 19757214 A | 6/1999 |
| DE | 10061420 A1 | 6/2002 |
| DE | 102011089357 A1 | 8/2012 |
| EP | 0414608 A1 | 2/1991 |
| EP | 0414608 A1 | 2/1991 |
| EP | 2724713 A1 | 4/2014 |
| FR | 2702144 A1 | 9/1994 |
| FR | 3033498 A1 | 9/2016 |
| KR | 20140003158 A | 1/2014 |
| WO | WO 2010/121919 | * 10/2010 |
| WO | 2013076061 A1 | 5/2013 |
| WO | 2014064121 A2 | 5/2014 |
| WO | 2015044390 A1 | 4/2015 |
| WO | 2016142551 A1 | 9/2016 |

* cited by examiner

OTHER PUBLICATIONS

International Search Report and Written Opinion dated Dec. 3, 2019 for corresponding PCT Application No. PCT/US2019/048447.

*Primary Examiner* — Tigabu Kassa
(74) *Attorney, Agent, or Firm* — POLSINELLI PC

(57) ABSTRACT

The present disclosure relates to hair-treatment compositions, typically in the form of an oil-in-water emulsion, comprising: (a) one or more monosaccharides with amine group(s); (b) one or more polysaccharides with amine group(s); wherein (a) and (b) are solubilized in an aqueous phase of the oil-in-water emulsion; (c) one or more oils; (d) one or more nonionic emulsifiers; and (e) water. The compositions strengthen hair fibers and provide additional cosmetic improvements to the hair such as conditioning, detangling, softness, suppleness, moisturizing, and manageability. Methods of treating hair with the compositions are also described. The methods include applying the composition to wet or damp hair, drying the hair (for example, with a blow dryer) and treating the hair with heat (for example, with a hot iron).

16 Claims, 4 Drawing Sheets

HAIR-TREATMENT COMPOSITIONS AND METHODS OF USE

FIELD OF THE DISCLOSURE

The present disclosure relates to hair-treatment compositions and methods for improving the strength and cosmetic attributes of hair.

BACKGROUND

Many hair styling and beautifying treatments have been developed to change the appearance of hair, including many chemical treatments. Chemical treatments include, for example, hair bleaching and coloring, permanents, waving products, and relaxing treatments (straightening treatments). These chemical treatments change the look of hair by changing its physical structure, which inevitably causes a certain degree of damage to the hair. Environmental factors, such as salt water, sunlight, and heat, are also known to damage hair. Damaged hair is characterized by unnatural changes to the protein structure of the individual hair strands or shafts. Damage results in split ends, dry straw-like hair, hair that is easily broken, and hair that is "frizzy" and unmanageable. Because the visible portion of hair is dead, it has no ability to regenerate itself. There are numerous over-the-counter and salon treatments that purport to repair damaged hair. These include conditioners, hot oil treatments, hydrolyzed proteins, vitamin formulations, and exotic fruit, leaf, or root extracts. These treatments, however, provide only limited improvement to the hair. Therefore, hair repair technologies that restore the properties of hair back to their natural level are desired.

SUMMARY OF THE DISCLOSURE

The hair-treatment compositions and methods of the instant disclosure provide advantageous effects to hair, such as strengthening of the hair fiber, protecting hair fibers from damage or further damage, improving cosmetic attributes including softness, shine, conditioning, and healthy appearance. The hair-treatment compositions include one or more monosaccharides with amine group(s) such as glucosamine, one or more polysaccharides with amine group(s) such as chitosan, and oils (natural, synthetic non-silicone oils, or silicone oils including amino silicone oils), which function in combination to treat damaged hair and restore its natural properties.

The hair-treatment compositions are typically in the form of an oil-in-water emulsion and include:
- (a) one or more monosaccharides with amine group(s);
- (b) one or more polysaccharides with amine group(s);
  - wherein (a) and (b) are solubilized in an aqueous phase of the oil-in-water emulsion;
- (c) one or more oils;
- (d) one or more nonionic emulsifiers; and
- (e) water.

The hair-treatment compositions typically have a pH of less than 7. This helps solubilize the one or more polysaccharides with amine groups in the water phase with the one or more monosaccharides with amine groups. The oil is emulsified with emulsifiers to create an oil-in-water emulsion.

Use of the hair-treatment compositions and methods for treating hair with the hair-treatment compositions include applying the composition to wet or damp hair, drying the hair (for example, with a blow dryer) and treating the hair with heat (for example, with a hot iron). The heat causes thermal activation of the hair-treatment compositions, which improves the adhesion and cohesion properties of films formed on the hair. The improved adhesion and cohesion properties result in long-lasting benefits to the hair that withstand shampooing. Thus, in some instances, the compositions are for use with a hot iron (e.g., a flat iron) for treating hair.

The hair-treatment compositions strengthen hair fibers and provide additional cosmetic improvements to the hair such as conditioning, detangling, softness, suppleness, moisturizing, and manageability.

BRIEF DESCRIPTION OF THE DRAWINGS

Implementations of the present technology will now be described, by way of example only, with reference to the attached figures, wherein.

Figure 1:
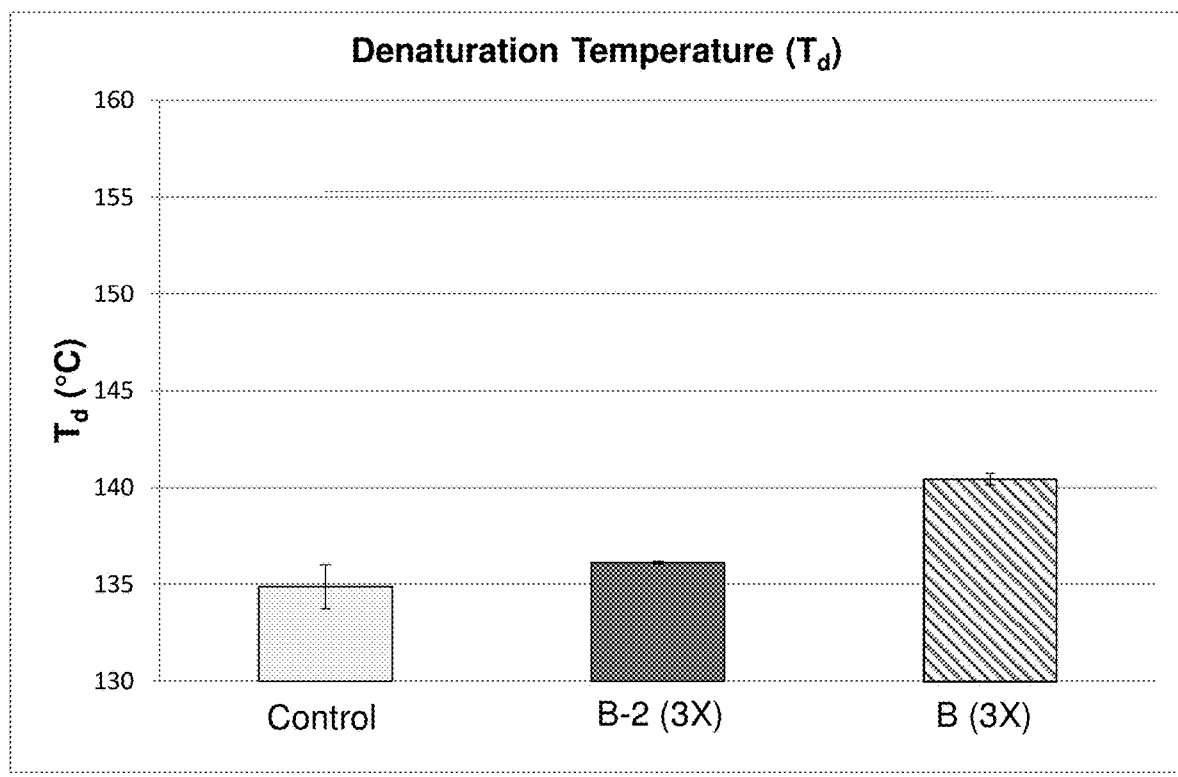
FIG. 1 graphically shows the denaturation temperature (Td) of untreated hair, hair treated with a comparative composition, and hair treated with an inventive composition.

It should be understood that the various aspects are not limited to the arrangements and instrumentality shown in the drawings.

DETAILED DESCRIPTION OF THE DISCLOSURE

The instant disclosure relates to hair-treatment compositions and to methods for treating hair using the hair-treatment compositions. The hair-treatment compositions are typically in the form of an oil-in-water emulsion and include:
- (a) about 0.01 to about 10 wt. % of one or more monosaccharides with amine group(s);
- (b) about 0.01 to about 10 wt. % of one or more polysaccharides with amine group(s);
  - wherein (a) and (b) are solubilized in an aqueous phase of the oil-in-water emulsion;
- (c) about 0.1 to about 20 wt. % of one or more oils;
- (d) 0.01 to about 20 wt. % of one or more nonionic emulsifiers; and
- (e) water;
  - wherein all weight percentages are based on the total weight of the compositions; and the composition has a pH of less than 7.

The pH may be about 2 to less than 7, about 3 to less than 7, about 2 to about 6, about 3 to about 6, or about 3, about 4, about 5, or about 6. In some instances, the hair treatment compositions may be free or essentially free of succinic acid, gluconic acid, derivatives thereof, and salts thereof.

The instant disclosure also relates to the use of the hair-treatment compositions described above (and throughout the disclosure) as a hair treatment, for example, for strengthening hair and for protecting hair from damage or further damage, and for improving cosmetic attributes of the hair, for example, imparting softness, shine, conditioning, and a healthy appearance to the hair. In some cases, the hair-treatment compositions of the instant disclosure are for use with heat, for example, with a hot iron (e.g., a flat iron) for the treatment of hair, for example, for strengthening hair and for protecting hair from damage or further damage, and for improving cosmetic attributes of the hair, for example, imparting softness, shine, conditioning, and a healthy appearance to the hair.

In addition to the description below, monosaccharides with amine group(s), polysaccharides with amine group(s), compositions comprising the monosaccharides and polysaccharides, and methods of using the monosaccharides and polysaccharides are described in French Application No. 1758048, filed on Aug. 31, 2017, which is incorporated herein by reference in its entirety.

(a) Monosaccharides with Amine Group(s)

The one or more monosaccharides with amine group(s) includes the organic or mineral acid salts thereof, the α or β anomers thereof, the optical isomers thereof of L or D configuration, and the solvates thereof such as hydrates. Preferably the monosaccharide(s) with amine group(s) of the invention are salified with the aid of a mineral acid such as hydrochloric acid.

In some cases, the monosaccharide) with amine group(s) include a mixture of monosaccharides with amine group(s), one of which is glucosamine or the salts thereof of an organic or mineral acid such as hydrochloric acid, the α or β anomers thereof, the optical isomers thereof of L or D configuration, and the solvates thereof such as hydrates.

In some instances, the monosaccharide(s) with amine group(s) includes a single monosaccharide with amine group(s), in particular glucosamine or the organic or mineral acid salts thereof or more particularly the mineral acid salts thereof such as the hydrochloric acid salt thereof, the α or β anomers thereof, the optical isomers thereof of L or D configuration, and the solvates thereof such as hydrates.

According to one particular embodiment, the monosaccharide(s) with amine group(s) are $C_5$ monosaccharides with amine group(s): pentosamines. According to this particular embodiment, the pentosamines are chosen from aldopentosamines and ketopentosamines such as xylosamine, arabinosamine, lyxosamine, ribosamine, ribulosamine and xylulosamine and also the organic or mineral acid salts thereof, the α or β anomers thereof, the optical isomers thereof of L or D configuration, and the solvates thereof such as hydrates.

According to another embodiment, the monosaccharide(s) with amine group(s) are $C_7$ monosaccharides with amine group(s): heptosamines such as aldoheptosamines and ketoheptosamines and also the organic or mineral acid salts thereof, and also the α or β anomers thereof, the optical isomers thereof of L or D configuration, and the solvates thereof such as hydrates.

According to a preferred embodiment, the monosaccharide(s) with amine group(s) are $C_6$ monosaccharides: hexosamines and also the organic or mineral acid salts thereof, the α or β anomers thereof, the optical isomers thereof of L or D configuration, and the solvates thereof such as hydrates.

As examples of monosaccharides with amine group(s), mention may be made of $C_6$ monosaccharides with amine group(s) or hexosamines: aldohexosamines and ketohexosamines. According to one embodiment, the hexosamines are chosen from glucosamine, galactosamine, allosamine, altrosamine, mannosamine, gulosamine, idosamine, galactosamine and talosamine, more particularly chosen from glucosamine and galactosamine, and also the salts thereof of an organic or mineral acid such as hydrochloric acid, the α or β anomers thereof, the optical isomers thereof of L or D configuration, and the solvates thereof such as hydrates, and more preferentially glucosamine, preferably of D configuration, preferably salified with a mineral acid such as hydrochloric acid.

Glucosamine ($C_6H_{13}NO_5$) is an abundant monosaccharide. It forms part of the structure of the polysaccharides chitosan and chitin, and can be commercially produced by the hydrolysis of crustacean exoskeletons and by fermentation of a grain such as corn or wheat. The neutral form of glucosamine or salts thereof can be used. Non-limiting examples of glucosamine salts include glucosamine chloride, glucosamine sulfate, glucosamine sulfate potassium, glucosamine sulfate potassium chloride, glucosamine hydrochloride, and N-acetylglucosamine.

In some instances, the monosaccharides with amine group(s) are selected from hexosamines of formula (A) and also the salts thereof of an organic or mineral acid such as hydrochloric acid, and also the α or β anomers thereof, the optical isomers thereof of L or D configuration, and the solvates thereof such as hydrates:

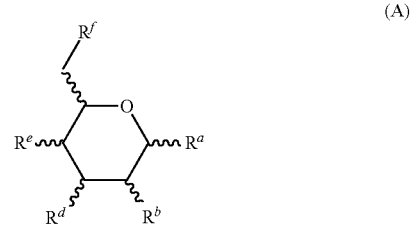

(A)

in which formula (A):

$R^a$, $R^b$, $R^d$, $R^e$ and $R^f$, which are identical or different, represent i) a hydroxyl group, ii) a ($C_1$-$C_4$)alkoxy group, the alkyl group of which may be optionally substituted, especially with one or more hydroxyl groups, iii) a carboxyl group, and iv) an $NR_1R_2$ group, with $R_1$ and $R_2$ as defined above, in particular $R_1$ and $R_2$ are chosen from a hydrogen atom and —C(O)—$R'_1$ with $R'_1$ being as defined above; preferably, $R_1$ and $R_2$ represent i) a hydrogen atom or ii) a —C(O)—$R'_1$ alkylcarbonyl group with $R'_1$ representing a ($C_1$-$C_4$) alkyl group such as methyl;

it being understood that at least one of the $R^a$, $R^b$, $R^d$, $R^e$ and $R^f$ radicals represents an $NR_1R_2$ group, preferably at least one of the $R^a$, $R^b$, $R^d$, $R^e$ and $R^f$ radicals represents an $NR_1R_2$ group and the radicals different from $NR_1R_2$ denote a hydroxyl group, more particularly $R^b$ represents an $NR_1R_2$ group such as $NH_2$ or —N(H)—C(O)—$R'_1$ with $R'_1$ representing a ($C_1$-$C_4$)alkyl group such as methyl, more particularly $NH_2$, and $R^a$, $R^d$, $R^e$ and $R^f$ represent a hydroxyl group.

Preferably, the compounds of formula (A) are of D configuration, also referred to as D-glucopyrans. The compounds of formula (A) are particularly of β (beta) anomeric configuration.

According to one particular embodiment, the monosaccharide(s) with amine group(s) are chosen from the compounds of formula (A') below and also the salts thereof of an organic or mineral acid, preferably a mineral acid such as hydrochloric acid, and also the α or β anomers thereof, the optical isomers thereof of L or D configuration, preferably D configuration, and the solvates thereof such as hydrates:

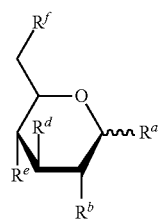

(A')

in which formula (A') $R^a$, $R^b$, $R^d$, $R^e$ and $R^f$ are as defined for (A) above.

The total amount of the monosaccharides having amine group(s) can vary but is typically about 0.01 to about 10 wt. %, based on the total weight of the hair-treatment composition. In some cases, the total amount of the monosaccharides having amine group(s) is about is about 0.01 to about 8 wt. %, about 0.01 to about 5 wt. %, about 0.01 to about 3 wt. %, about 0.05 to about 10 wt. %, about 0.05 to about 8 wt. %, about 0.05 to about 5 wt. %, about 0.05 to about 3 wt. %, about 0.1 to about 10 wt. %, about 0.1 to about 8 wt. %, about 0.1 to about 5 wt. %, about 0.1 to about 3 wt. %, about 0.5 to about 10 wt. %, about 0.5 to about 8 wt. %, about 0.5 to about 5 wt. %, about 0.5 to about 3 wt. %, or about 0.5 to about 2 wt. %, including ranges and subranges there between, based on the total weight of the hair-treatment composition.

(b) Polysaccharides with Amine Group(s)

The polysaccharides with amine group(s) include organic or mineral acid salts thereof, the α or β anomers thereof, the optical isomers thereof of L or D configuration, and the solvates thereof such as hydrates.

In some cases, the polysaccharide(s) with amine group(s) have an average molecular weight MW of less than or equal to 400 kDa, particularly less than 200 kDa. Similarly, in some cases, the polysaccharide(s) with amine group(s) have a low average molecular weight MW i.e. have an MW<100 kDa, preferentially have an average MW which is <40 kDa, more preferentially have an average MW which is between 1 kDa and 30 kDa inclusive, more preferentially still have an average MW which is between 3 kDa and 28 kDa inclusive.

The polysaccharide(s) with amine group(s) may be natural, of animal or plant origin, or derived from synthesis, hemisynthesis or biosynthesis.

According to one particular embodiment, the polysaccharide(s) with amine group(s) are chosen from those with $C_5$-$C_7$ saccharide units and also the organic or mineral acid salts thereof, the α or β anomers thereof, the optical isomers thereof of L or D configuration, and the solvates thereof such as hydrates.

More particularly, the polysaccharide(s) with amine group(s) may be a $C_6$ saccharide unit with amine group(s), these polysaccharides with amine group(s) are then referred to as polyhexosamines.

According to one particular embodiment, the saccharide units of the polysaccharide with amine group(s) are of β (beta) anomeric configuration and/or D configuration.

According to one particular embodiment, the saccharide units of the polysaccharide with amine group(s) are joined to one another between the C1 carbon atoms of one saccharide unit and the C4 carbon atoms of the other saccharide unit, denoted (1→4), such as the polysaccharide with amine group(s) of formula (B) below, and also the organic or mineral acid salts thereof, the α or β anomers thereof, the optical isomers thereof of L or D configuration, and the solvates thereof such as hydrates:

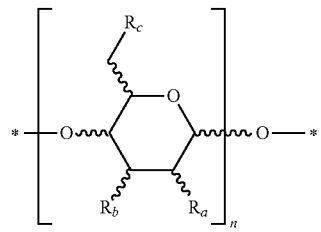

(B)

in which formula (B):

the $R_a$, $R_b$, $R_c$ radicals of each saccharide unit may be identical or different;

n is an integer greater than or equal to 2, particularly between 3 and 3000 inclusive, and more particularly between 5 and 2500, preferentially between 10 and 2300;

$R_a$, $R_b$, and $R_c$, which are identical or different, represent i) a hydroxyl group, ii) a ($C_1$-$C_4$)alkoxy group, the alkyl group of which may be optionally substituted, especially with one or more hydroxyl groups, iii) a carboxyl group, and iv) an $NR_1R_2$ group, with $R_1$ and $R_2$ as defined above, in particular $R_1$ and $R_2$ are chosen from a hydrogen atom and —C(O)—R'$_1$ in which R'$_1$ is as defined above; preferably $R_1$ and $R_2$ represent i) a hydrogen atom or ii) —C(O)—R'$_1$ with R'$_1$ representing a ($C_1$-$C_4$)alkyl group such as methyl;

it being understood that at least one of the $R_a$, $R_b$ or $R_c$ radicals of at least one saccharide unit represents an $NR_1R_2$ group and that at least one of the $NR_1R_2$ groups of at least one saccharide unit represents an $NH_2$ group; preferably $R_a$ of at least one saccharide unit represents an $NR_1R_2$ group with $R_1$ which represents a hydrogen atom and $R_2$ is chosen from i) a hydrogen atom or ii) a —C(O)—R'$_1$ group, and $R_b$ and $R_e$ represent a hydroxyl group, it being understood that at least one of the $NR_1R_2$ groups of at least one saccharide unit represents an $NH_2$ group.

More particularly, the polysaccharide(s) with amine group(s) are of formula ($B_1$) below, and also the organic or mineral acid salts thereof, the α or β anomers thereof, the optical isomers thereof of L or D configuration, and the solvates thereof such as hydrates:

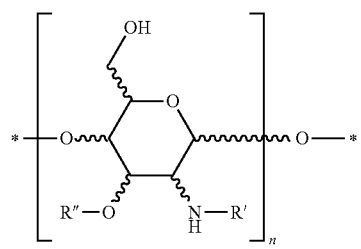

($B_1$)

in which formula ($B_1$):

R' represents a hydrogen atom or a ($C_1$-$C_4$)alkylcarbonyl group such as acetyl $CH_3$—C(O)—;

R" represents a hydrogen atom or a ($C_1$-$C_4$)alkyl group optionally substituted with a carboxyl group such as —CH($CO_2H$)—$CH_3$;

n is an integer greater than or equal to 2, particularly between 3 and 3000 inclusive, more particularly between 5 and 2500, preferentially between 10 and 2300;

it being understood that in the polysaccharide ($B_1$) at least one saccharide unit bears an $NH_2$ amino group and at least one other saccharide unit bears at least one N(H)—R' group with R' representing a ($C_1$-$C_4$)alkylcarbonyl group such as acetyl $CH_3$—C(O)—.

Preferably, the saccharide units of formula (B) or ($B_1$) are of D configuration, also referred to as D-glucopyran. The units of formula (B) or ($B_1$) are particularly of β (beta) anomeric configuration. According to one particular embodiment, the polysaccharides of the invention are chosen from the compounds of formula ($B_2$) below and also the organic or mineral acid salts thereof, and the solvates thereof such as hydrates:

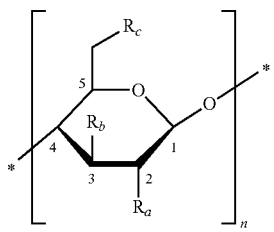

(B$_2$)

in which formula ($B_2$):

$R_a$, $R_b$, and $R_c$, are as defined for (B) above; and the $R_a$, $R_b$, $R_c$ radicals of each saccharide unit may be identical or different;

n is an integer greater than or equal to 2, particularly between 3 and 3000 inclusive, more particularly between 5 and 2500, preferentially between 10 and 2300;

it being understood that in the polysaccharide ($B_2$) at least one of the $R_a$, $R_b$ or $R_c$ radicals of at least one saccharide unit represents an $NR_1R_2$ group and that at least one of the $NR_1R_2$ groups of at least one saccharide unit represents an $NH_2$ group; preferably at least one saccharide unit bears an $R_a$ amino $NH_2$ group and at least one other saccharide unit bears an $R_a$ group which represents —N(H)—R' with R' representing a ($C_1$-$C_4$)alkylcarbonyl group such as acetyl $CH_3$—C(O)—.

Preferentially, the polysaccharide(s) with amine group(s) are chosen from chitin and chitosan and their derivatives, preferably chitosan. Chitosan can vegetable sourced (commercially known by the tradename of KIONUTRIME CSG, supplied by the company Kitozymeor), or derived, for example, by treating the chitin shells of shrimp and other crustaceans with an alkaline substance, like sodium hydroxide.

More particularly, the polysaccharide(s) with amine group(s) are chosen from those of formula ($B_3$) below, and also the organic or mineral acid salts thereof, and the solvates thereof such as hydrates:

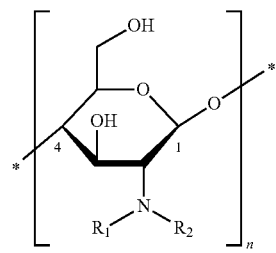

(B$_3$)

in which formula ($B_3$):

$R_1$ and $R_2$ are as defined in the formula (B), ($B_1$) or ($B_2$); and n is an integer greater than or equal to 2, particularly between 3 and 3000 inclusive, more particularly between 5 and 2500, preferentially between 10 and 2300;

it being understood that in the polysaccharide of formula ($B_3$) at least one saccharide unit bears an $NH_2$ amino group and at least one other saccharide unit bears an N(H)—R' group with R' representing a ($C_1$-$C_4$)alkylcarbonyl group such as acetyl $CH_3$—C(O)—.

More particularly, the polysaccharide(s) with amine group(s) are chosen from chitosans of formula ($B_4$) below, and also the organic or mineral acid salts thereof, and the solvates thereof such as hydrates:

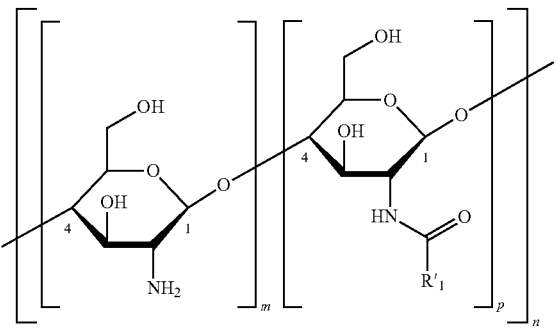

(B$_4$)

in which formula ($B_4$):

$R'_1$ representing a ($C_1$-$C_4$)alkyl group such as methyl; and n is an integer greater than or equal to 2, particularly between 3 and 3000 inclusive, more particularly between 5 and 2500, preferentially between 10 and 2300;

P is greater than 0 and ranges up to 0.5, preferably from 0.05 to 0.3, and better still from 0.1 to 0.20 such as 0.15 with m+p being equal to 1;

it being understood that in the chitosan at least one saccharide unit bears an $NH_2$ amino group and at least one other saccharide unit bears an N(H)—$R'_1$ group with R' representing a ($C_1$-$C_4$)alkylcarbonyl group such as acetyl $CH_3$—C(O)—.

For example, when m=0.7, p=0.3 this means that 70% of the amine groups are free (unsubstituted) and 30% of the amino groups are N-alkyl($C_1$-$C_4$)carbonyl groups, in particular N-acetyl groups, corresponding to the chitosan of formula:

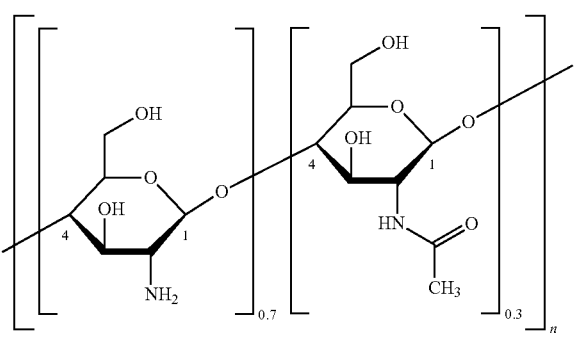

with n as defined above.

In some instances, the polysaccharide(s) with amine group(s) are chosen from chitosans, salified using organic acid, preferentially using monocarboxylic acid of formula (I) as defined above or polycarboxylic acid of formula (II) as defined above, more preferentially still salified using carboxylic acid of formula (I) such as lactic acid.

In some cases, the polysaccharide(s) with amine group(s) refers to a mixture of polysaccharide(s) with amine group(s), one of which is a chitosan or the organic or mineral acid salts thereof, preferably the salts thereof of an organic acid such as lactic acid, the α or β anomers thereof, the optical isomers thereof of L or D configuration, and the solvates thereof such as hydrates. Alternatively, the polysaccharide(s) with amine group(s) may relate to a single polysaccharide with amine group(s), in particular a mixture of chitosan or the organic or mineral salts thereof or more particularly the organic acid salts thereof such as the lactic acid salt thereof, the α or β anomers thereof, the optical isomers thereof of L or D configuration, and the solvates thereof such as hydrates.

According to another embodiment, the polysaccharide(s) with amine group(s) denotes a single polysaccharide with amine group(s), in particular a chitosan or the organic or mineral acid salts thereof or more particularly the organic acid salts thereof such as the lactic acid salt thereof, the α or β anomers thereof, the optical isomers thereof of L or D configuration, and the solvates thereof such as hydrates.

The total amount of polysaccharides with amine group(s) in the hair treatment composition may vary but is typically about 0.01 to about 10 wt. %, based on the total weight of the hair-treatment composition. In some cases, the total amount of polysaccharides with amine group(s) is about is about 0.01 to about 8 wt. %, about 0.01 to about 5 wt. %, about 0.01 to about 3 wt. %, about 0.05 to about 10 wt. %, about 0.05 to about 8 wt. %, about 0.05 to about 5 wt. %, about 0.05 to about 3 wt. %, about 0.1 to about 10 wt. %, about 0.1 to about 8 wt. %, about 0.1 to about 5 wt. %, about 0.1 to about 3 wt. %, about 0.5 to about 10 wt. %, about 0.5 to about 8 wt. %, about 0.5 to about 5 wt. %, about 0.5 to about 3 wt. %, or about 0.5 to about 2 wt. %, including ranges and subranges there between, based on the total weight of the hair-treatment composition.

The weight ratio of the total amount of the monosaccharides with amine group(s) (a) to the total amount of polysaccharides with amine group(s) (b) may vary but it typically about 10:1 to about 1:10. In some instances, the weight ratio is about 8:1 to about 1:8, about 5:1 to about 1:5, about 4:1 to about 1:4, about 3:1 to about 1:3, or about 2:1 to about 1:2, including ranges and subranges there between.

(c) Oils

The hair treatment compositions include one or more oils, for example, oils selected from natural oils and silicone oils, including amino silicone oils (e.g., silicone polymers with primary amine functionality). These oils provide and enhance conditioning attributes and improve manageability of the hair. Non-limiting examples of natural oils include those of plant origin such as palm oil, soybean oil, olive oil, coconut oil, and a mixture thereof. Non-limiting examples of silicones include dimethiconol, dimethicone, and a mixture thereof. Non-limiting examples of amino silicone oils include amodimethicone, aminoethylaminopropyl dimethicone, aminopropyl dimethicone, and a mixture thereof. While not wishing to be bound by any particular theory, it is believed that the amino functional groups of the amino silicone polymers undergo reactive synergies with the monosaccharides with amine group(s) such as glucosamine and the polysaccharides with amine group(s) such as chitosan.

The incorporation of oils into the hair-treatment composition is enhanced by using emulsifiers, in particular, nonionic emulsifiers. The emulsifiers can be added to the hair-treatment composition or can be provided together with the oil as pre-emulsified raw material (for example, an amino silicone emulsion).

When a natural oil such as olive oil or palm oil, is employed, the oil can be emulsified according to a balance of emulsifiers to match the Hydrophilic-Lipophilic Balance (HLB) value of the oil. Non-limiting examples of natural oils include palm oil (HLB=8), soybean oil (HLB=7), olive oil (HLB=7), and coconut oil (HLB=8). In some instances, when using natural oils in the hair-treatment compositions, it can be useful to include at least one emulsifier with an HLB of greater than 10 and at least one emulsifier with an HLB of less than 5. The total amount of these emulsifiers can be such that the final HLB of the hair-treatment composition is within +/−0.5 of the HLB of the natural oil in the hair treatment composition. This typically results in the final HLB of the emulsified natural oil in the hair-treatment composition ranging from about 6 to about 8. A more exhaustive but non-limiting list of natural oils that may be included in the hair-treatment compositions is provided later, under the heading "Natural Oils."

When a silicone oil, such as amino silicone oil, is employed, the silicone oil can be emulsified in situ or added as a pre-emulsified oil. In some cases, amino silicone oils with high molecular weight and charge density, and a droplet size of not more than 50 microns are utilized. This results in the hair treatment compositions providing: (i) a high levels of conditioning, (ii) substantivity, (iii) film uniformity, and (iv) reactive synergies with monosaccharides having amine group(s) (such as glucosamine) and polysaccharides having amine group(s) (such as chitosan) with minimal transfer and greasy feel. A more exhaustive but non-limiting list of silicones that can be included in the hair treatment compositions is provided later, under the heading, "Silicone Oils."

The total amount of oil in the hair treatment composition can vary but is typically about 0.1 to about 20 wt. %, based on the total weight of the hair treatment composition. In some instances, the total amount of oil is about 0.1 to about 15 wt. %, about 0.1 to about 10 wt. %, about 0.5 to about 20 wt. %, about 0.5 to about 15 wt. %, or about 0.5 to about 10 wt. %, including ranges and subranges there between, based on the total weight of the hair-treatment composition.

(d) Nonionic Emulsifiers

Emulsifiers are used to incorporate the oil into the hair treatment composition by forming an emulsion. The hair-treatment compositions preferably include one or more nonionic emulsifiers. Additional emulsifiers, however, can also be included (or excluded), such as amphoteric, anionic, and/or cationic emulsifiers.

For O/W emulsions, examples of emulsifiers that may be mentioned include nonionic emulsifiers such as oxyalkylenated (more particularly polyoxyethylenated) fatty acid esters of glycerol; oxyalkylenated fatty acid esters of sorbitan; oxyalkylenated (oxyethylenated and/or oxypropylenated) fatty acid esters; oxyalkylenated (oxyethylenated and/or oxypropylenated) fatty alcohol ethers; sugar esters such as sucrose stearate; and mixtures thereof. A more exhaustive but non-limiting list of useful nonionic emulsifiers is provided later, under the heading "Nonionic Emulsifiers."

In some cases it is preferable that hair treatment compositions containing natural oils include two or more nonionic emulsifiers. In particular, one or more nonionic emulsifier having an HLB of 10 or higher and one or more nonionic emulsifiers having an HLB of 5 or less. The total amount of these emulsifiers can be such that the final HLB of the hair-treatment composition is within +/−0.5 of the HLB of the natural oil in the hair treatment composition. This typically results in the final HLB of the emulsified natural oil in the hair-treatment composition ranging from about 6 to about 8.

The total amount of nonionic emulsifiers in the hair-treatment composition can vary but is typically about 0.01 to about 20 wt. %, based on the total weight of the hair treatment composition. In some instances, the total amount of nonionic emulsifiers is about 0.01 to about 15 wt. %, about 0.01 to about 10 wt. %, about 0.01 to about 5 wt. %, about 0.1 to about 20 wt. %, about 0.1 to about 15 wt. %, about 0.1 to about 10 wt. %, about 0.1 to about 5 wt. %, about 0.5 to about 20 wt. %, about 0.5 to about 15 wt. %, about 0.5 to about 10 wt. %, about 0.5 to about 5 wt. %, or about 0.5 to about 3 wt. %, including ranges and subranges there between, based on the total weight of the hair treatment composition.

(e) Water

The total amount of water in the hair-treatment compositions can vary but is typically about 50 to 98 wt. %, based on the total weight of the hair treatment composition. In some instances, the total amount of water is about 60 wt. % to about 98 wt. %, about 70 wt. % to about 98 wt. %, about 75 wt. % to about 98 wt. %, including ranges and subranges there between, based on the total weight of the hair treatment composition.

The hair treatment compositions are useful for strengthening hair and for protecting hair from damage or further damage, and improving cosmetic attributes of the hair, for example, imparting softness, shine, conditioning, and a healthy appearance to the hair. Methods of treating the hair typically include applying a hair treatment composition to the hair. The hair treatment composition can be applied to wet or damp hair, but can also be applied to dry hair. The hair may be freshly shampooed and optionally conditioned prior to application of the hair treatment composition. Shampooing and optionally conditioning the hair immediately before application of the hair treatment composition helps ensure that the hair is not contaminated with dirt, etc., prior to treatment.

After application of the hair treatment composition to the hair, the hair may be dried, for example, the hair may be dried with a blow dryer or may be allowed to dry naturally. After drying the hair, or during the drying process, the hair is treated with heat. Heat causes thermal activation of the hair-treatment compositions, which improves the adhesion and cohesion properties of films formed on the hair. The improved adhesion and cohesion properties result in long-lasting benefits to the hair that withstand shampooing. The hair is heated to a temperature of 80° C. or higher, for example, to a temperature of about 100 to about 250° C. In some cases, the hair is heated to a temperature of about 125 to about 250° C., about 150 to about 250° C., or about 100 to about 225° C., about 125 to about 225° C., about 150 to about 225° C., or about 160 to about 225° C., including ranges and subranges there between.

The hair may be heated, for example, using a hot iron (e.g., a curling iron or a flat iron), which typically heats to a temperature of about 110° C. to about 230° C. The hot iron can be run along the length of the hair one or more times in order to heat the hair and thermally activate the elements of the hair-treatment composition on the hair, thereby forming/strengthening films on the hair. The process of applying a hair treatment composition to the hair, drying the hair, and heating the hair, can be repeated multiple times. The process can be carried out once, twice, three times, four times, five times, or more, during a single treatment (a single treatment occurs during a single day, for example, during a single session at home or at a salon. Repeating the process multiple times allows for the build-up of thicker, stronger films on the hair.

In one embodiment, a method for treating hair includes:
(i) applying a hair-treatment composition of the instant disclosure to the hair, which may be wet, damp, or dry;
(ii) drying the hair, for example, with a blow dryer;
(iii) after applying the hair-treatment composition to the hair and drying the hair, heating the hair to a temperature above room temperature, for example, with a hot iron, to a temperature of 80° C. or higher, preferably a temperature of about 100° C. to about 250° C., more preferably, a temperature of about 150° C. to about 225° C.; and
(iv) optionally, repeating (i)-(iii) multiple times in a single treatment.

The instant disclosure also relates to the use of the hair-treatment compositions described above (and throughout the disclosure) for use in the treatment of hair, in particular, hair of the head (hair on the top of the head, not the eyebrows and eyelashes). The compositions can be used for strengthening hair and for protecting hair from damage or further damage, and improving cosmetic attributes of the hair, for example, imparting softness, shine, conditioning, and a healthy appearance to the hair. Thus, in some cases, the instant disclosure relates to a hair-treatment composition for strengthening hair and for protecting hair from damage or further damage, and improving cosmetic attributes of the hair, for example, imparting softness, shine, conditioning, and a healthy appearance to the hair, wherein the hair treatment composition comprises:

(a) about 0.01 to about 10 wt. %, preferably about 0.05 to about 8 wt. %, more preferably, about 0.5 to about 5 wt. % of one or more hexosamines of formula (A) or formula (A'), for example, glucosamine and/or a salt thereof;

(b) about 0.01 to about 10 wt. %, preferably about 0.05 to about 8 wt. %, more preferably about 0.5 to about 5 wt. % of one or more polyhexosamines of formula (B), formula ($B_1$), formula ($B_2$), formula ($B_3$), or formula ($B_4$), for example, chitosan;

wherein (a) and (b) are solubilized in an aqueous phase of the oil-in-water emulsion and the ratio of (a) to (b) is about 3:1 to about 1:3;

(c) about 0.1 to about 20 wt. %, preferably about 0.05 to about 15 wt. %, more preferably about 0.5 to about 10 wt. % of one or more oils;

(d) 0.01 to about 20 wt. %, preferably about 0.05 to about 15 wt. %, more preferably about 0.5 to about 10 wt. % of one or more nonionic emulsifiers; and (e) about 50 to about 98 wt. %, preferably about 60 to about 98 wt. %, more preferably about 70 to about 98 wt. % of water;

(g) optionally, one or more water-soluble solvents; wherein all weight percentages are based on the total weight of the compositions; and the composition has a pH of less than 7, preferably a pH of about 3 to less than 7, more preferably a pH of about 3 to about 6.

For instance, the hair-treatment compositions are for use with a hot iron (include a flat iron) for the treatment of hair, in particular, for protecting hair from damage or further damage, and improving cosmetic attributes of the hair, for example, imparting softness, shine, conditioning, and a healthy appearance to the hair.

In one embodiment, the hair treatment composition is in the form of an oil-in-water emulsion and includes:

(a) about 0.01 to about 10 wt. %, preferably about 0.05 to about 8 wt. %, more preferably, about 0.5 to about 5 wt. % of one or more hexosamines of formula (A) or formula (A'), for example, glucosamine and/or a salt thereof;

(b) about 0.01 to about 10 wt. %, preferably about 0.05 to about 8 wt. %, more preferably about 0.5 to about 5 wt. % of one or more polyhexosamines of formula (B), formula ($B_1$), formula ($B_2$), formula ($B_3$), or formula ($B_4$), for example, chitosan;
wherein (a) and (b) are solubilized in an aqueous phase of the oil-in-water emulsion and the ratio of (a) to (b) is about 3:1 to about 1:3;

(c) about 0.1 to about 20 wt. %, preferably about 0.05 to about 15 wt. %, more preferably about 0.5 to about 10 wt. % of one or more oils;

(d) 0.01 to about 20 wt. %, preferably about 0.05 to about 15 wt. %, more preferably about 0.5 to about 10 wt. % of one or more nonionic emulsifiers; and (e) about 50 to about 98 wt. %, preferably about 60 to about 98 wt. %, more preferably about 70 to about 98 wt. % of water;

(g) optionally, one or more water-soluble solvents; wherein all weight percentages are based on the total weight of the compositions; and the composition has a pH of less than 7, preferably a pH of about 3 to less than 7, more preferably a pH of about 3 to about 6.

In one embodiment, the hair treatment composition is in the form of an oil-in-water emulsion and includes:

(a) about 0.01 to about 10 wt. %, preferably about 0.05 to about 8 wt. %, more preferably, about 0.5 to about 5 wt. % of one or more hexosamines of formula (A) or formula (A'), for example, glucosamine and/or a salt thereof;

(b) about 0.01 to about 10 wt. %, preferably about 0.05 to about 8 wt. %, more preferably about 0.5 to about 5 wt. % of one or more polyhexosamines of formula (B), formula ($B_1$), formula ($B_2$), formula ($B_3$), or formula ($B_4$), for example, chitosan;
wherein (a) and (b) are solubilized in an aqueous phase of the oil-in-water emulsion and the ratio of (a) to (b) is about 3:1 to about 1:3;

(c) about 0.1 to about 20 wt. %, preferably about 0.05 to about 15 wt. %, more preferably about 0.5 to about 10 wt. % of one or more natural oils, for example, one or more natural oils of plant original such as palm oil, soybean oil, olive oil, coconut oil, and a mixture thereof;

(d) 0.01 to about 20 wt. %, preferably about 0.05 to about 15 wt. %, more preferably about 0.5 to about 10 wt. % of two or more nonionic emulsifiers, wherein the nonionic emulsifiers comprise:
one or more nonionic emulsifier having an HLB of 10 or higher; and
one or more nonionic emulsifiers having an HLB of 5 or less; and (e) about 50 to about 98 wt. %, preferably about 60 to about 98 wt. %, more preferably about 70 to about 98 wt. % of water;

(g) optionally, one or more water-soluble solvents; wherein all weight percentages are based on the total weight of the compositions; and the composition has a pH of less than 7, preferably a pH of about 3 to less than 7, more preferably a pH of about 3 to about 6.

In one embodiment, the hair treatment composition is in the form of an oil-in-water emulsion and includes:

(a) about 0.01 to about 10 wt. %, preferably about 0.05 to about 8 wt. %, more preferably, about 0.5 to about 5 wt. % of one or more hexosamines of formula (A) or formula (A'), for example, glucosamine and/or a salt thereof;

(b) about 0.01 to about 10 wt. %, preferably about 0.05 to about 8 wt. %, more preferably about 0.5 to about 5 wt. % of one or more polyhexosamines of formula (B), formula ($B_1$), formula ($B_2$), formula ($B_3$), or formula ($B_4$), for example, chitosan;
wherein (a) and (b) are solubilized in an aqueous phase of the oil-in-water emulsion and the ratio of (a) to (b) is about 3:1 to about 1:3;

(c) about 0.1 to about 20 wt. %, preferably about 0.05 to about 15 wt. %, more preferably about 0.5 to about 10 wt. % of one or more amino silicones, for example, amodimethicone, aminoethylaminopropyl dimethicone, aminopropyl dimethicone, and a mixture thereof;

(d) 0.01 to about 20 wt. %, preferably about 0.05 to about 15 wt. %, more preferably about 0.5 to about 10 wt. % of two or more nonionic emulsifiers, wherein the nonionic emulsifiers comprise:

(e) about 50 to about 98 wt. %, preferably about 60 to about 98 wt. %, more preferably about 70 to about 98 wt. % of water;

(g) optionally, one or more water-soluble solvents; wherein all weight percentages are based on the total weight of the compositions; and the composition has a pH of less than 7, preferably a pH of about 3 to less than 7, more preferably a pH of about 3 to about 6.

Additional non-limiting lists of components useful in the hair-treatment compositions of the instant disclosure are provided below.

Non-Silicone Oils

Examples of non-silicone oils include: hydrocarbon-based oils of plant origin, such as perhydrosqualene, liquid triglycerides of fatty acids comprising from 4 to 10 carbon atoms, such as heptanoic or octanoic acid triglycerides, or alternatively, for example, sunflower oil, maize oil, soybean oil, marrow oil, grapeseed oil, sesame seed oil, hazelnut oil, apricot kernel oil, macadamia oil, arara oil, coriander oil, castor oil, avocado oil, caprylic/capric acid triglycerides, such as those sold by the company Stearineries Dubois or those sold under the names MIGLYOL 810, 812 and 818 by the company Dynamit Nobel, jojoba oil and shea butter oil; synthetic esters and ethers, especially of fatty acids and/or of fatty alcohols, for instance the oils of formulae $R^1COOR^2$ and $R^1OR^2$ in which $R^1$ represents a fatty acid residue containing from 7 to 29 carbon atoms and $R^2$ represents a branched or unbranched hydrocarbon-based chain containing from 3 to 30 carbon atoms, for instance purcellin oil, isononyl isononanoate, isopropyl myristate, isopropyl palmitate, 2-ethylhexyl palmitate, 2-octyldodecyl stearate, isocetyl stearate, 2-octyldodecyl erucate or isostearyl isostearate; hydroxylated esters, for instance isostearyl lactate, octyl hydroxystearate, octyldodecyl hydroxystearate, diisostearyl malate, triisocetyl citrate, and fatty alkyl heptanoates, octanoates and decanoates; polyol esters, for instance propylene glycol dioctanoate, neopentyl glycol diheptanoate and diethylene glycol diisononanoate; and pentaerythritol esters, for instance pentaerythrityl tetraisostearate; volatile or non-volatile, linear or branched hydrocarbons, of mineral or synthetic origin, and derivatives thereof, other than the branched alkanes comprising from 8 to 18 carbon atoms, such as liquid petroleum jelly and hydrogenated polyisobutene such as PARLEAM oil; volatile linear alkanes comprising from 7 to 17 carbon atoms such as undecane or tridecane; fatty alcohols that are liquid at room temperature, containing from 8 to 26 carbon atoms, for instance octyldodecanol, 2-butyloctanol, 2-hexyldecanol, 2-undecylpentadecanol or oleyl alcohol.

As examples of linear alkanes that are suitable for use in the invention, mention may be made of n-heptane (C7), n-octane (C8), n-nonane (C9), n-decane (C10), n-undecane (C11), n-dodecane (C12), n-tridecane (C13) and n-tetradecane (C14), and mixtures thereof. According to a particular embodiment, the volatile linear alkane is chosen from n-nonane, n-undecane, n-dodecane, n-tridecane and n-tetradecane, and mixtures thereof.

Non-limiting examples of liquid triglycerides and oils of plant origin include alexandria laurel tree oil, avocado oil, apricot stone oil, barley oil, borage seed oil, calendula oil, canelle nut tree oil, canola oil, caprylic/capric triglyceride castor oil, coconut oil, corn oil, cotton oil, cottonseed oil, evening primrose oil, flaxseed oil, groundnut oil, hazelnut oil, glycereth triacetate, glycerol triheptanoate, glyceryl trioctanoate, glyceryl triundecanoate, hempseed oil, jojoba oil, lucerne oil, maize germ oil, marrow oil, millet oil, neopentylglycol dicaprylate/dicaprate, olive oil, palm oil, passionflower oil, pentaerythrityl tetrastearate, poppy oil, propylene glycol ricinoleate, rapeseed oil, rye oil, safflower oil, sesame oil, shea butter, soya oil, soybean oil, sweet almond oil, sunflower oil, sysymbrium oil, syzigium aromaticum oil, tea tree oil, walnut oil, wheat germ glycerides and wheat germ oil.

The use of natural oils can be particularly preferred, for instance, natural oils of plant origin, such as amaranth seed oil, apricot kernel oil, argan oil, avocado oil, babassu oil, cottonseed oil, borage seed oil, camelina oil, thistle oil, peanut oil, pomegranate seed oil, grapefruit seed oil, hemp oil, hazelnut oil, elderberry seed oil, currant seed oil, jojoba oil, linseed oil, macadamia nut oil, corn oil, almond oil, marula oil, evening primrose oil, olive oil, palm oil, palm kernel oil, Brazil nut oil, pecan nut oil, peach kernel oil, rapeseed oil, castor oil, sea buckthorn pulp oil, sea buckthorn kernel oil, sesame oil, soy bean oil, sunflower oil, grape seed oil, walnut oil, wild rose oil, wheat germ oil, and the liquid components of coconut oil, and the like. In one embodiment, the oil is a plant oil selected from palm oil, soybean oil, olive oil, coconut oil, and a mixture thereof.

Silicone Oils

The compositions of the present disclosure may further comprise one or more silicone oils. The one or more silicone oils may be chosen from amino silicone oils (e.g., amodimethicone) and non-amino silicones (e.g., dimethicone) and mixtures thereof.

In an embodiment, the one or more silicone oils of the present disclosure is an amino silicone oil. The term "amino silicone" is intended to mean any silicone comprising at least one primary, secondary or tertiary amine or a quaternary ammonium group (i.e., a quaternized group).

Useful amino silicones include the following:

a) polysiloxanes corresponding to formula (A):

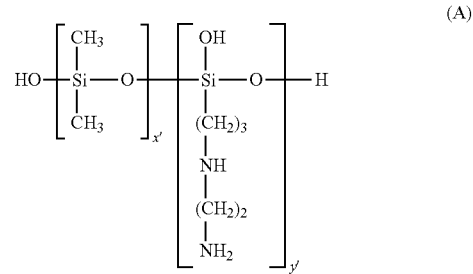

in which x' and y' are integers such that the weight-average molecular weight (Mw) is comprised between about 5000 and 500 000;

b) amino silicones corresponding to formula (B):

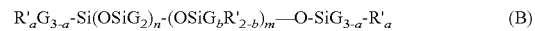

in which:
G, which may be identical or different, designate a hydrogen atom, or a phenyl, OH or $C_1$-$C_8$ alkyl group, for example methyl, or $C_1$-$C_8$ alkoxy, for example methoxy,
a, which may be identical or different, denote the number 0 or an integer from 1 to 3, in particular 0;
b denotes 0 or 1, and in particular 1;
m and n are numbers such that the sum (n+m) ranges from 1 to 2000 and in particular from 50 to 150, it being possible for n to denote a number from 0 to 1999 and in particular from 49 to 149, and for m to denote a number from 1 to 2000 and in particular from 1 to 10;
R', which may be identical or different, denote a monovalent radical having formula —$C_qH_{2q}L$ in which q is a number ranging from 2 to 8 and L is an optionally quaternized amino group chosen from the following groups:
—NR"-Q-N(R")$_2$
—N(R")$_2$
—N+(R")$_3$A-
—N+H(R")$_2$A-
—N+H$_2$(R")A-
—N(R")-Q-N+R"H$_2$A-
—NR"-Q-N+(R")$_2$HA-
—NR"-Q-N+(R")$_3$A-,
in which R", which may be identical or different, denote hydrogen, phenyl, benzyl, or a saturated monovalent hydrocarbon-based radical, for example a $C_1$-$C_{20}$ alkyl radical; Q denotes a linear or branched $C_rH_{2r}$ group, r being an integer ranging from 2 to 6, preferably from 2 to 4; and A- represents a cosmetically acceptable ion, in particular a halide such as fluoride, chloride, bromide or iodide.

A group of amino silicones corresponding to this definition (B) is represented by the silicones called "trimethylsilylamodimethicone" having formula (C):

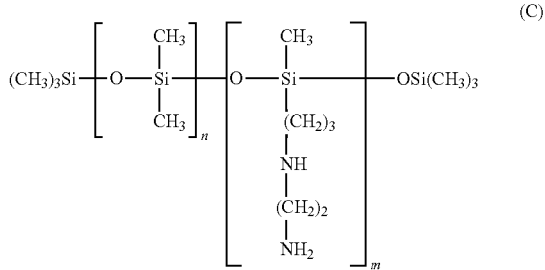

in which n and m have the meanings given above, in formula B.

Another group of amino silicones corresponding to this definition is represented by silicones having the following formulae (D) or (E):

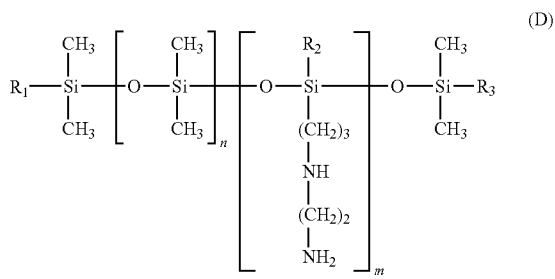

in which:

m and n are numbers such that the sum (n+m) can range from 1 to 1000, in particular from 50 to 250 and more particularly from 100 to 200, it being possible for n to denote a number from 0 to 999 and in particular from 49 to 249, and more particularly from 125 to 175, and for m to denote a number from 1 to 1000 and in particular from 1 to 10, and more particularly from 1 to 5;

$R_1$, $R_2$, $R_3$, which may be identical or different, represent a hydroxy or $C_1$-$C_4$ alkoxy radical, where at least one of the radicals $R_1$ to $R_3$ denotes an alkoxy radical.

The alkoxy radical is preferably a methoxy radical.

The hydroxy/alkoxy mole ratio ranges preferably from 0.2:1 to 0.4:1 and preferably from 0.25:1 to 0.35:1 and more particularly equals 0.3:1.

The weight-average molecular weight (Mw) of the silicone ranges preferably from 2000 to 1 000 000, more particularly from 3500 to 200 000.

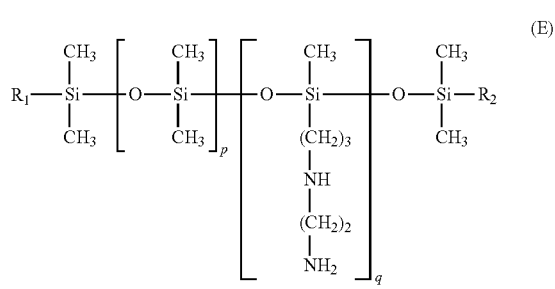

in which:

p and q are numbers such that the sum (p+q) ranges from 1 to 1000, particularly from 50 to 350, and more particularly from 150 to 250; it being possible for p to denote a number from 0 to 999 and in particular from 49 to 349, and more particularly from 159 to 239 and for q to denote a number from 1 to 1000, in particular from 1 to 10, and more particularly from 1 to 5;

$R_1$, $R_2$, which may be the same or different, represent a hydroxy or $C_1$-$C_4$ alkoxy radical, where at least one of the radicals $R_1$ or $R_2$ denotes an alkoxy radical.

The alkoxy radical is preferably a methoxy radical.

The hydroxy/alkoxy mole ratio ranges generally from 1:0.8 to 1:1.1 and preferably from 1:0.9 to 1:1 and more particularly equals 1:0.95.

The weight-average molecular weight (Mw) of the silicone ranges preferably from 2000 to 200 000, even more particularly 5000 to 100 000 and more particularly from 10 000 to 50 000.

Commercial products corresponding to these silicones having structure (D) or (E) may include in their composition one or more other amino silicones whose structure is different than formulae (D) or (E).

Particularly preferred amodimethicone products containing amino silicones having structure (D) are sold by Wacker under the name BELSIL ADM 652, BELSIL ADM 4000 E, or BELSIL ADM LOG 1.

A product containing amino silicones having structure (E) is sold by Wacker under the name FLUID WR 1300.

When these amino silicones are used, one particularly advantageous embodiment consists in using them in the form of an oil-in-water emulsion. The oil-in-water emulsion may comprise one or more surfactants. The surfactants may be of any nature but are preferably cationic and/or nonionic. The number-average size of the silicone particles in the emulsion generally ranges from 3 nm to 500 nanometres. Preferably, in particular as amino silicones having formula (E), microemulsions are used whose average particle size ranges from 5 nm to 60 nanometres (limits included) and more preferably from 10 nm to 50 nanometres (limits included). Accordingly, according to the invention the microemulsions of amino silicone having formula (E) sold as Finish CT 96 E® or SLM 28020® by Wacker can be used.

Another group of amino silicones corresponding to this definition is represented by the following formula (F):

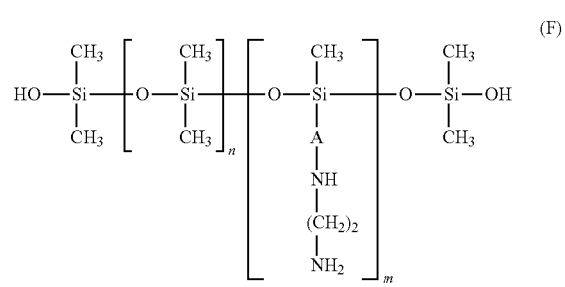

in which:
  m and n are numbers such that the sum (n+m) ranges from 1 to 2000 and in particular from 50 to 150, it being possible for n to denote a number from 0 to 1999 and in particular from 49 to 149, and for m to denote a number from 1 to 2000 and in particular from 1 to 10;
  A denotes a linear or branched alkylene radical containing from 4 to 8 carbon atoms and preferably 4 carbon atoms. This radical is preferably linear.

The weight-average molecular weight (Mw) of these amino silicones ranges preferably from 2000 to 1 000 000 and even more particularly from 3500 to 200 000.

A preferred silicone of formula (F) is amodimethicone (INCI name) sold under the tradename XIAMETER® MEM-8299 Cationic Emulsion by Dow Corning.

Another group of amino silicones corresponding to this definition is represented by the following formula (G):

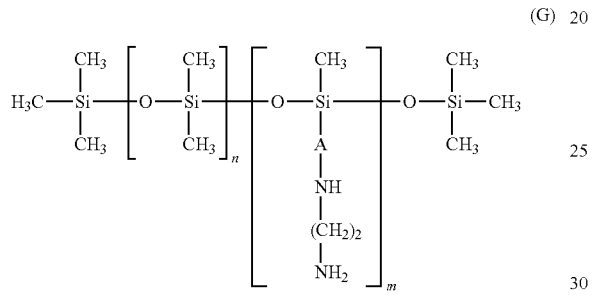

in which:
  m and n are numbers such that the sum (n+m) ranges from 1 to 2000 and in particular from 50 to 150, it being possible for n to denote a number from 0 to 1999 and in particular from 49 to 149, and for m to denote a number from 1 to 2000 and in particular from 1 to 10;
  A denotes a linear or branched alkylene radical containing from 4 to 8 carbon atoms and preferably 4 carbon atoms. This radical is preferably branched.

The weight-average molecular weight (Mw) of these amino silicones ranges preferably from 500 to 1 000 000 and even more particularly from 1000 to 200 000.

A silicone having this formula is for example DC2-8566 Amino Fluid by Dow Corning.

c) amino silicones corresponding to formula (H):

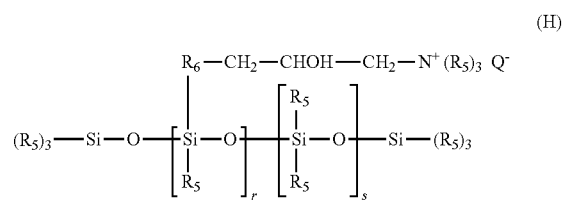

in which:
  $R_5$ represents a monovalent hydrocarbon-based radical containing from 1 to 18 carbon atoms, and in particular a $C_1$-$C_{18}$ alkyl or $C_2$-$C_{18}$ alkenyl radical, for example methyl;
  $R_6$ represents a divalent hydrocarbon-based radical, in particular a $C_1$-$C_{18}$ alkylene radical or a divalent $C_1$-$C_{18}$, for example C1-$C_8$, alkylenoxy radical linked to the Si via an SiC bond;
  Q- is an anion such as a halide ion, in particular chloride, or an organic acid salt (for example acetate);
  r represents a mean statistical value from 2 to 20 and in particular from 2 to 8;
  s represents a mean statistical value from 20 to 200 and in particular from 20 to 50.

Such amino silicones are described more particularly in U.S. Pat. No. 4,185,087.

d) quaternary ammonium silicones having formula (I):

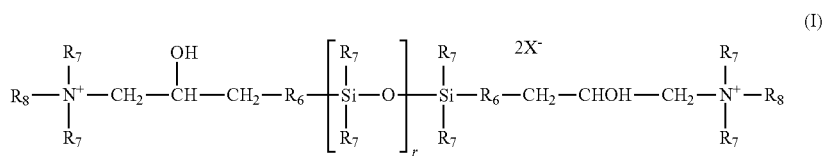

in which:
  $R_7$, which may be identical or different, represent a monovalent hydrocarbon-based radical containing from 1 to 18 carbon atoms, and in particular a C1-$C_{18}$ alkyl radical, a $C_2$-$C_{18}$ alkenyl radical or a ring containing 5 or 6 carbon atoms, for example methyl;
  $R_6$ represents a divalent hydrocarbon-based radical, in particular a C1-$C_{18}$ alkylene radical or a divalent C1-$C_{18}$, for example $C_1$-$C_8$, alkylenoxy radical linked to the Si via an SiC bond;
  $R_8$, which may be identical or different, represent a hydrogen atom, a monovalent hydrocarbon-based radical containing from 1 to 18 carbon atoms, and in particular a $C_1$-$C_{18}$ alkyl radical, a $C_2$-$C_{18}$ alkenyl radical or a —$R_6$—$NHCOR_7$ radical;
  X- is an anion such as a halide ion, in particular chloride, or an organic acid salt (for example acetate);

r represents a mean statistical value from 2 to 200 and in particular from 5 to 100;

These silicones are described, for example, in patent application EP-A 0 530 974.

e) amino silicones having formula (J):

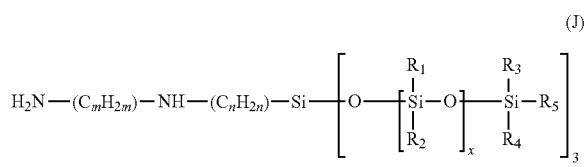

in which:
- $R_1$, $R_2$, $R_3$ and $R_4$, which may be identical or different, denote a $C_1$-$C_4$ alkyl radical or a phenyl group;
- $R_5$ denotes a $C_1$-$C_4$ alkyl radical or a hydroxyl group;
- n is an integer ranging from 1 to 5;
- m is an integer ranging from 1 to 5;
- and in which x is chosen such that the amine number is between 0.01 and 1 meq/g;

f) multiblockpolyoxyalkylenated amino silicones, of type (AB)n, A being a polysiloxane block and B being a polyoxyalkylenated block containing at least one amine group.

Said silicones are preferably constituted of repeating units having the following general formulae:

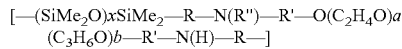

or alternatively

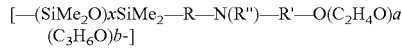

in which:
- a is an integer greater than or equal to 1, preferably ranging from 5 to 200, more particularly ranging from 10 to 100;
- b is an integer comprised between 0 and 200, preferably ranging from 4 to 100, more particularly between from 5 and 30;
- x is an integer ranging from 1 to 10 000, more particularly from 10 to 5000;
- R" is a hydrogen atom or a methyl;
- R, which may be identical or different, represent a divalent linear or branched $C_2$-$C_{12}$ hydrocarbon-based radical, optionally including one or more heteroatoms such as oxygen; preferably, R denotes an ethylene radical, a linear or branched propylene radical, a linear or branched butylene radical, or a —CH$_2$CH$_2$CH$_2$OCH(OH)CH$_2$— radical; preferentially R denotes a —CH$_2$CH$_2$CH$_2$OCH(OH)CH$_2$— radical;
- R', which may be identical or different, represent a divalent linear or branched $C_2$-$C_{12}$ hydrocarbon-based radical, optionally including one or more heteroatoms such as oxygen; preferably, R' denotes an ethylene radical, a linear or branched propylene radical, a linear or branched butylene radical, or a —CH$_2$CH$_2$CH$_2$OCH(OH)CH$_2$— radical; preferentially R' denotes —CH(CH$_3$)—CH$_2$—.

The siloxane blocks preferably represent between 50 and 95 mol % of the total weight of the silicone, more particularly from 70 to 85 mol %.

The amine content is preferably between 0.02 and 0.5 meq/g of copolymer in a 30% solution in dipropylene glycol, more particularly between 0.05 and 0.2.

The weight-average molecular weight (Mw) of the silicone oil is preferably comprised between 5000 and 1 000 000, more particularly between 10 000 and 200 000.

Mention may be made especially of the silicones sold under the names Silsoft™ A-843 or Silsoft™ A+ by Momentive.

g) the alkylamino silicones corresponding to formula (K) below:

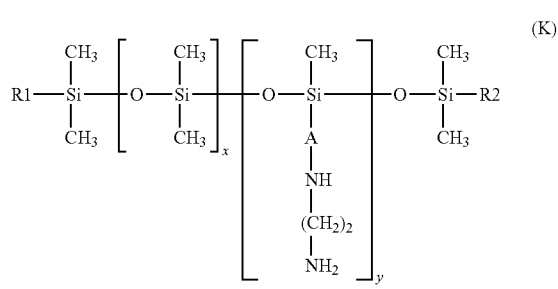

in which:
- x and y are numbers ranging from 1 to 5000; preferably, x ranges from 10 to 2000 and especially from 100 to 1000; preferably, y ranges from 1 to 100;
- $R_1$ and $R_2$, which may be identical or different, preferably identical, are linear or branched, saturated or unsaturated alkyl radicals, comprising 6 to 30 carbon atoms, preferably 8 to 24 carbon atoms and especially 12 to 20 carbon atoms;
- A denotes a linear or branched alkylene radical containing from 2 to 8 carbon atoms,
- Preferably, A comprises 3 to 6 carbon atoms, especially 4 carbon atoms; preferably, A is branched. Mention may be made especially of the following divalent radicals: —CH$_2$CH$_2$CH$_2$— and —CH$_2$CH(CH$_3$)CH$_2$—.
- Preferably, R1 and R2, which may be identical or different, are saturated linear alkyl radicals comprising 6 to 30 carbon atoms, preferably 8 to 24 carbon atoms and especially 12 to 20 carbon atoms; mention may be made in particular of dodecyl, tetradecyl, pentadecyl, hexadecyl, heptadecyl, octadecyl, nonadecyl and eicosyl radicals; and preferentially, R1 and R2, which may be identical or different, are chosen from hexadecyl (cetyl) and octadecyl (stearyl) radicals.

Preferentially, the silicone oil is of formula (K) with:
- x ranging from 10 to 2000 and especially from 100 to 1000;
- y ranging from 1 to 100;
- A comprising 3 to 6 carbon atoms and especially 4 carbon atoms; preferably, A is branched; and more particularly A is chosen from the following divalent radicals: CH$_2$CH$_2$CH$_2$ and —CH$_2$CH(CH$_3$)CH$_2$—; and
- $R_1$ and $R_2$, which may be identical or different, being linear, saturated alkyl radicals comprising 6 to 30 carbon atoms, preferably 8 to 24 carbon atoms and especially 12 to 20 carbon atoms; chosen in particular from dodecyl, tetradecyl, pentadecyl, hexadecyl, heptadecyl, octadecyl, nonadecyl and eicosyl radicals; preferentially, $R_1$ and $R_2$, which may be identical or different, being chosen from hexadecyl (cetyl) and octadecyl (stearyl) radicals.

A preferred silicone oil of formula (K) is bis-cetearylamodimethicone (INCI name).

Mention may be made especially of the silicone products sold under the name Silsoft™ AX by Momentive.

h) silicone oils with at least one quaternary ammonium group. Suitable non-limiting examples are quaternium 80, silicone quaternium-1, silicone quaternium-2, silicone quaternium-2 panthenol succinate, silicone quaternium-3, silicone quaternium-4, silicone quaternium-5, silicone quaternium-6, silicone quaternium-7, silicone quaternium-8, silicone quaternium-9, silicone quaternium-10, silicone quaternium-11, silicone quaternium-12, silicone quaternium-15, silicone quaternium-16, silicone quaternium-16/Glycidoxy Dimethicone Crosspolymer, silicone quaternium-17, silicone quaternium-18, silicone quaternium-20 and silicone quaternium-21. Preferred are quaternium 80, silicone quaternium-16, silicone quaternium-18, silicone quaternium-1, silicone quaternium-2, silicone quaternium-3, silicone quaternium-4, silicone quaternium-5, silicone quaternium-6, silicone quaternium-7, silicone quaternium-8, silicone quaternium-9, silicone quaternium-10, silicone quaternium-11, silicone quaternium-12, silicone quaternium-15, silicone quaternium-17, silicone quaternium-20 and silicone quaternium-21. More preferred are quaternium 80, silicone quaternium-16, silicone quaternium-18, silicone quaternium-3, silicone quaternium-4, silicone quaternium-5, silicone quaternium-6, silicone quaternium-7, silicone quaternium-8, silicone quaternium-9, silicone quaternium-10, silicone quaternium-11, silicone quaternium-12, silicone quaternium-15, and silicone quaternium-17. Preferred are quaternium 80, silicone quaternium-16, silicone quaternium-18, silicone quaternium-15, and mixtures thereof.

The silicone oils with at least one quaternary ammonium group can also include those compounds of formula (B) when L in formula (B) is a quaternized amino group as described.

In an embodiment, the one or more silicone oils of the present disclosure is a non-amino silicone oil such as a dimethicone.

In an embodiment, the one or more silicone oils of the present disclosure is an amino silicone oil such as amodimethicone.

The silicone oil of the present disclosure may be provided or may be commercially available in emulsion form that further comprises emulsifiers chosen from nonionic emulsifiers, cationic emulsifiers, and mixtures thereof. In certain embodiments, the emulsion in which the silicone oil is contained is a microemulsion.

Nonionic Emulsifiers

Examples of nonionic emulsifiers that may be used are fatty alcohols, alpha-diols and (C1-C24)alkylphenols, these compounds being alkoxylated, polyethoxylated, polypropoxylated and/or polyglycerolated, and containing at least one fatty chain comprising, for example, from 8 to 18 carbon atoms, it being possible for the number of ethylene oxide and/or propylene oxide groups to especially range from 2 to 50, and for the number of glycerol groups to especially range from 2 to 30.

Mention may also be made of copolymers of ethylene oxide and propylene oxide, optionally oxyethylenated sorbitan fatty acid esters, sucrose fatty acid esters, polyoxyalkylenated fatty acid esters, polyoxyalkylenated fatty amides, optionally oxyalkylenated alkyl(poly)glucosides, alkylglucoside esters, derivatives of N-alkylglucamine and of N-acylmethylglucamine, aldobionamides, amine oxides and (poly)oxyalkylenated silicones. Suitable examples are oleth-10, oleth-20, laureth-12, trideceth-5, trideceth-10, steareth-20, and mixtures thereof.

Other examples of nonionic emulsifiers that may be used are fatty alcohols such as stearyl alcohol, isostearyl alcohol, cetearyl alcohol, cetyl alcohol, lauryl alcohol, decyl alcohol, and mixtures thereof.

The nonionic emulsifiers can also be chosen from monooxyalkylenated or polyoxyalkylenated and monoglycerolated or polyglycerolated nonionic emulsifiers, and alkyl (poly)glucosides. The oxyalkylene units are more particularly oxyethylene or oxypropylene units, or a combination thereof, preferably oxyethylene units.

Useful nonionic emulsifiers may include: oxyalkylenated (C8-C24)alkylphenols; saturated or unsaturated, linear or branched, oxyalkylenated C8-C40 alcohols; saturated or unsaturated, linear or branched, oxyalkylenated C8-C30 amides; esters of saturated or unsaturated, linear or branched, C8-C30 acids and of polyethylene glycols; saturated or unsaturated, oxyethylenated plant oils; condensates of ethylene oxide and/or of propylene oxide, alone or as mixtures; oxyethylenated and/or oxypropylenated silicones; and alkyl(poly)glucosides.

As examples of monoglycerolated or polyglycerolated nonionic emulsifiers, monoglycerolated or polyglycerolated C8-C40 alcohols are useable. In particular, the monoglycerolated or polyglycerolated C C8-C40 alcohols correspond to formula (A1) below:

$$R_{29}O-[CH_2-CH(CH_2OH)-O]_m-H \quad (A1)$$

in which formula (A1):

$R_{29}$ represents a linear or branched $C_8$-$C_{40}$ and preferably $C_8$-$C_{30}$ alkyl or alkenyl radical; and m represents a number ranging from 1 to 30, or from 1 to 10.

As examples of compounds of formula (A1), mention may be made of lauryl alcohol containing 4 mol of glycerol (INCI name: Polyglyceryl-4 Lauryl Ether), lauryl alcohol containing 1.5 mol of glycerol, oleyl alcohol containing 4 mol of glycerol (INCI name: Polyglyceryl-4 Oleyl Ether), oleyl alcohol containing 2 mol of glycerol (INCI name: Polyglyceryl-2 Oleyl Ether), cetearyl alcohol containing 2 mol of glycerol, cetearyl alcohol containing 6 mol of glycerol, oleocetyl alcohol containing 6 mol of glycerol, and octadecanol containing 6 mol of glycerol.

The alcohol of formula (A1) may represent a mixture of alcohols in the same way that the value of m represents a statistical value, which means that, in a commercial product, several species of polyglycerolated fatty alcohols may coexist in the form of a mixture.

The alkyl(poly)glycoside nonionic emulsifer(s) may be represented by formula (A2) below:

$$R_{30}O-(R_{31}O)_t(G)_v \quad (A2)$$

in which:

$R_{30}$ represents a saturated or unsaturated, linear or branched alkyl group comprising from about 8 to 24 carbon atoms, or an alkylphenyl group in which the linear or branched alkyl group comprises from 8 to 24 carbon atoms;

$R_{31}$ represents an alkylene group containing from about 2 to 4 carbon atoms, G represents a saccharide unit comprising from 5 to 6 carbon atoms, t denotes a value ranging from 0 to 10, or from 0 to 4, and v denotes a value ranging from 1 to 15.

In some cases, the alkyl(poly)glycoside nonionic emulsifier(s) correspond to formula (A2) in which:

$R_{30}$ denotes a linear or branched, saturated or unsaturated alkyl group containing from 8 to 18 carbon atoms, G denotes glucose, fructose or galactose, preferably glucose, t denotes a value ranging from 0 to 3, and is preferably equal to 0, and $R_{31}$ and v are as defined previously.

The degree of polymerization of the alkyl(poly)glucoside nonionic emulsifier(s), as represented, for example, by the index v in formula (A2), ranges on average from 1 to 15, or from 1 to 4. This degree of polymerization more particularly ranges from 1 to 2 and better still from 1.1 to 1.5, on average.

The glycoside bonds between the saccharide units are of 1.6 or 1.4 type and preferably of 1.4 type.

Examples of compounds of formula (A2) that may especially be mentioned are decyl glucoside, coco-glucoside, lauryl glucoside, such as the products sold by the company Cognis under the names PLANTAREN (600 CS/U, 1200 and 2000) or PLANTACARE (818, 1200 and 2000). Use may also be made of the products sold by the company SEPPIC under the names TRITON CG 110 (or ORAMIX CG 110) and Triton CG 312 (or ORAMIX NS 10), the products sold by the company BASF under the name LUTENSOL GD 70 or the products sold by the company Chem Y under the name AG 10 LK. Use may also be made, for example, of the 1,4-(C8-C16)alkylpolyglucoside as an aqueous solution at 53% by weight relative to the total weight of the solution, sold by Cognis under the reference PLANTACARE 818 UP.

The fatty acid esters of a sugar that can be used as nonionic amphiphilic lipids can be chosen in particular from the group comprising esters or mixtures of esters of a $C_8$-$C_{22}$ fatty acid and of sucrose, of maltose, of glucose or of fructose, and esters or mixtures of esters of a $C_{14}$-$C_{22}$ fatty acid and of methylglucose.

The $C_8$-$C_{22}$ or $C_{14}$-$C_{22}$ fatty acids forming the fatty unit of the esters that can be used in the emulsion comprise a saturated or unsaturated linear alkyl chain having, respectively, from 8 to 22 or from 14 to 22 carbon atoms. The fatty unit of the esters can be chosen in particular from stearates, behenates, arachidonates, palmitates, myristates, laurates, caprates and mixtures thereof.

By way of example of esters or of mixtures of esters of a fatty acid and of sucrose, of maltose, of glucose or of fructose, mention may be made of sucrose monostearate, sucrose distearate, sucrose tristearate and mixtures thereof, such as the products sold by the company Croda under the name Crodesta F50, F70, F110 and F160 having, respectively, an HLB (Hydrophilic Lipophilic Balance) of 5, 7, 11 and 16; and, by way of example of esters or of mixtures of esters of a fatty acid and of methylglucose, mention may be made of the distearate of methylglucose and of polyglycerol-3, sold by the company Goldschmidt under the name Tego-care 450. Mention may also be made of glucose monoesters or maltose monoesters, such as methyl O-hexadecanoyl-6-D-glucoside and O-hexadecanoyl-6-D-maltoside.

The fatty alcohol ethers of a sugar that can be used as nonionic amphiphilic lipids can be chosen in particular form the group comprising ethers or mixtures of ethers of a $C_8$-$C_{22}$ fatty alcohol and of glucose, of maltose, of sucrose or of fructose, and ethers or mixtures of ethers of a $C_{14}$-$C_{22}$ fatty alcohol and of methylglucose. They are in particular alkylpolyglucosides.

The $C_8$-$C_{22}$ or $C_{14}$-$C_{22}$ fatty alcohols forming the fatty unit of the ethers that can be used in the emulsion of the instant disclosure comprise a saturated or unsaturated linear alkyl chain having, respectively, from 8 to 22 or from 14 to 22 carbon atoms. The fatty unit of the ethers can be chosen in particular from decyl, cetyl, behenyl, arachidyl, stearyl, palmityl, myristyl, lauryl, capryl and hexadecanoyl units, and mixtures thereof such as cetearyl.

By way of example of fatty alcohol ethers of a sugar, mention may be made of alkylpolyglucosides, such as decylglucoside and laurylglucoside sold, for example, by the company Henkel under the respective names Plantaren 2000 and Plantaren 1200, cetostearylglucoside, optionally as a mixture with cetostearyl alcohol, sold, for example, under the name Montanov 68 by the company Seppic, under the name Tego-care CG90 by the company Goldschmidt and under the name Emulgade KE3302 by the company Henkel, and also arachidylglucoside, for example in the form of the mixture of arachidyl and behenyl alcohols and of arachidylglucoside sold under the name Montanov 202 by the company Seppic.

Use is more particularly made, as nonionic amphiphilic lipid of this type, of sucrose monostearate, sucrose distearate, sucrose tristearate and mixtures thereof, the distearate of methylglucose and of polyglycerol-3, and alkylpolyglucosides.

The glycerol fatty esters that can be used as nonionic amphiphilic lipids can be chosen in particular from the group comprising the esters formed from at least one acid comprising a saturated linear alkyl chain having from 16 to 22 carbon atoms, and from 1 to 10 glycerol units. Use may be made of one or more of these glycerol fatty esters in the emulsion of the instant disclosure.

These esters may be chosen in particular from stearates, behenates, arachidates, palmitates and mixtures thereof. Stearates and palmitates are preferably used.

By way of example of a surfactant that can be used in the emulsion of the instant disclosure, mention may be made of decaglycerol monostearate, distearate, tristearate and pentastearate (10 glycerol units) (CTFA names: polyglyceryl-10 stearate, polyglyceryl-10 distearate, polyglyceryl-10 tristearate, polyglyceryl-10 pentastearate), such as the products sold under the respective names Nikkol Decaglyn 1-S, 2-S, 3-S and 5-S by the company Nikko, and diglyceryl monostearate (CTFA name: polyglyceryl-2 stearate) such as the product sold by the company Nikko under the name Nikkol DGMS.

The sorbitan fatty esters that can be used as nonionic amphiphilic lipids chosen in particular from the group comprising esters of a $C_{16}$-$C_{22}$ fatty acid and of sorbitan and oxyethylenated esters of a $C_{16}$-$C_{22}$ fatty acid and of sorbitan. They are formed from at least one fatty acid comprising at least one saturated linear alkyl chain, having, respectively, from 16 to 22 carbon atoms, and from sorbitol or from ethoxylated sorbitol. The oxyethylenated esters generally comprise from 1 to 100 ethylene oxide units, and preferably from 2 to 40 ethylene oxide (EO) units.

These esters can be chosen in particular from stearates, behenates, arachidates, palmitates and mixtures thereof. Stearates and palmitates are preferably used.

By way of example of sorbitan fatty ester and of an oxyethylenated sorbitan fatty ester, mention may be made of sorbitan monostearate (CTFA name: sorbitan stearate) sold by the company ICI under the name Span 60, sorbitan monopalmitate (CTFA name: sorbitan palmitate) sold by the company ICI under the name Span 40, or sorbitan 20 EO tristearate (CTFA name: polysorbate 65) sold by the company ICI under the name Tween 65.

The ethoxylated fatty ethers are typically ethers made up of 1 to 100 ethylene oxide units and of at least one fatty alcohol chain having from 16 to 22 carbon atoms. The fatty chain of the ethers can be chosen in particular from behenyl, arachidyl, stearyl and cetyl units, and mixtures thereof, such as cetearyl. By way of example of ethoxylated fatty ethers, mention may be made of ethers of behenyl alcohol comprising 5, 10, 20 and 30 ethylene oxide units (CTFA names: beheneth-5, beheneth-10, beheneth-20 and beheneth-30), such as the products sold under the names Nikkol BB5, BB10, BB20 and BB30 by the company Nikko, and the ether of stearyl alcohol comprising 2 ethylene oxide units (CTFA name: steareth-2), such as the product sold under the name Brij 72 by the company ICI.

The ethoxylated fatty esters that can be used as nonionic amphiphilic lipids are esters made up of 1 to 100 ethylene oxide units and of at least one fatty acid chain comprising from 16 to 22 carbon atoms. The fatty chain of the esters can be chosen in particular from stearate, behenate, arachidate and palmitate units, and mixtures thereof. By way of example of ethoxylated fatty esters, mention may be made of the ester of stearic acid comprising 40 ethylene oxide units, such as the product sold under the name Myrj 52 (CTFA name: PEG-40 stearate) by the company ICI, and the ester of behenic acid comprising 8 ethylene oxide units (CTFA name: PEG-8 behenate), such as the product sold under the name Compritol HD5 ATO by the company Gattefosse.

The block copolymers of ethylene oxide and of propylene oxide that can be used as nonionic amphiphilic can be chosen in particular from poloxamers and in particular from Poloxamer 231, such as the product sold by the company ICI under the name Pluronic L81 of formula (V) with x=z=6, y=39 (HLB 2); Poloxamer 282, such as the product sold by the company ICI under the name Pluronic L92 of formula (V) with x=z=10, y=47 (HLB 6); and Poloxamer 124, such as the product sold by the company ICI under the name Pluronic L44 of formula (V) with x=z=11, y=21 (HLB 16).

As nonionic amphiphilic lipids, mention may also be made of the mixtures of nonionic emulsifiers described in document EP-A-705593, incorporated herein for reference.

Suitable hydrophobically-modified emulsifiers include, for example, inulin lauryl carbamate, commercially available from Beneo Orafti under the tradename Inutec SP1.

In one embodiment, the nonionic emulsifiers are selected from stearyl alcohol, steareth-20, glyceryl stearate, trideceth-5, trideceth-10, and a mixture thereof.

Water-Soluble Solvents

The hair-treatment compositions may optionally include one or more water-soluble solvents. The term "water-soluble solvent" is interchangeable with the term "water-miscible solvent" and means a compound that is liquid at 25° C. and at atmospheric pressure (760 mmHg), and it has a solubility of at least 50% in water under these conditions. In some cases, the water-soluble solvent has a solubility of at least 60%, 70%, 80%, or 90%. Non-limiting examples of water-soluble solvents include, for example, glycerin, alcohols (for example, $C_{1-30}$, $C_{1-15}$, $C_{1-10}$, or $C_{1-4}$ alcohols), organic solvents, polyols (polyhydric alcohols), glycols (e.g., butylene glycol, caprylyl glycol, etc.), and a mixture thereof.

As examples of organic solvents, non-limiting mentions can be made of monoalcohols and polyols such as ethyl alcohol, isopropyl alcohol, propyl alcohol, benzyl alcohol, and phenylethyl alcohol, or glycols or glycol ethers such as, for example, monomethyl, monoethyl and monobutyl ethers of ethylene glycol, propylene glycol or ethers thereof such as, for example, monomethyl ether of propylene glycol, butylene glycol, hexylene glycol, dipropylene glycol as well as alkyl ethers of diethylene glycol, for example monoethyl ether or monobutyl ether of diethylene glycol. Other suitable examples of organic solvents are ethylene glycol, propylene glycol, butylene glycol, hexylene glycol, propane diol, and glycerin. The organic solvents can be volatile or non-volatile compounds.

Further non-limiting examples of water-soluble solvents include alkanediols such as glycerin, 1,2,6-hexanetriol, trimethylolpropane, ethylene glycol, propylene glycol, diethylene glycol, triethylene glycol, tetraethylene glycol, pentaethylene glycol, dipropylene glycol, 2-butene-1,4-diol, 2-ethyl-1,3-hexanediol, 2-methyl-2,4-pentanediol, (caprylyl glycol), 1,2-hexanediol, 1,2-pentanediol, and 4-methyl-1,2-pentanediol; alkyl alcohols having 1 to 4 carbon atoms such as ethanol, methanol, butanol, propanol, and isopropanol; glycol ethers such as ethylene glycol monomethyl ether, ethylene glycol monoethyl ether, ethylene glycol monobutyl ether, ethylene glycol monomethyl ether acetate, diethylene glycol monomethyl ether, diethylene glycol monoethyl ether, diethylene glycol mono-n-propyl ether, ethylene glycol mono-iso-propyl ether, diethylene glycol mono-iso-propyl ether, ethylene glycol mono-n-butyl ether, ethylene glycol mono-t-butyl ether, diethylene glycol mono-t-butyl ether, 1-methyl-1-methoxybutanol, propylene glycol monomethyl ether, propylene glycol monoethyl ether, propylene glycol mono-t-butyl ether, propylene glycol mono-n-propyl ether, propylene glycol mono-iso-propyl ether, dipropylene glycol monomethyl ether, dipropylene glycol monoethyl ether, dipropylene glycol mono-n-propyl ether, and dipropylene glycol mono-iso-propyl ether; 2-pyrrolidone, N-methyl-2-pyrrolidone, 1,3-dimethyl-2-imidazolidinone, formamide, acetamide, dimethyl sulfoxide, sorbit, sorbitan, acetine, diacetine, triacetine, sulfolane, and a mixture thereof.

Polyhydric alcohols are useful. Examples of polyhydric alcohols include glycerin, ethylene glycol, diethylene glycol, triethylene glycol, propylene glycol, dipropylene glycol, tripropylene glycol, 1,3-butanediol, 2,3-butanediol, 1,4-butanediol, 3-methyl-1,3-butanediol, 1,5-pentanediol, tetraethylene glycol, 1,6-hexanediol, 2-methyl-2,4-pentanediol, polyethylene glycol, 1,2,4-butanetriol, 1,2,6-hexanetriol, and a mixture thereof. Polyol compounds may also be used. Non-limiting examples include the aliphatic diols, such as 2-ethyl-2-methyl-1,3-propanediol, 3,3-dimethyl-1,2-butanediol, 2,2-diethyl-1,3-propanediol, 2-methyl-2-propyl-1,3-propanediol, 2,4-dimethyl-2,4-pentanediol, 2,5-dimethyl-2,5-hexanediol, 5-hexene-1,2-diol, and 2-ethyl-1,3-hexanediol, and a mixture thereof.

Implementation of the present disclosure is provided by way of the following examples. The examples serve to illustrate the technology without being limiting in nature.

Example 1

| | (Inventive Compositions with Natural Oils) | | | | |
|---|---|---|---|---|---|
| | INCI US | A | B | C | D |
| Glucosamine | GLUCOSAMINE HCl | 1 | 1 | 1 | 1 |
| Chitosan | CHITOSAN | 1 | 1 | 1 | 1 |
| Oils | GLYCINE SOJA (SOYBEAN) OIL | | | | 1 |
| | OLEA EUROPAEA (OLIVE) FRUIT OIL | | 1 | | |
| | COCOS NUCIFERA (COCONUT) OIL | 1 | | | |
| | ELAEIS GUINEENSIS (PALM) OIL | | | 1 | |
| Nonionic | STEARYL ALCOHOL | 0.2 | 0.1 | 0.2 | 0.1 |
| Emulsifiers | STEARETH-20 | 0.2 | 0.1 | 0.2 | 0.1 |

-continued (Inventive Compositions with Natural Oils)

| | INCI US | A | B | C | D |
|---|---|---|---|---|---|
| | GLYCERYL STEARATE | 0.7 | 0.8 | 0.7 | 0.8 |
| pH Adjust | LACTIC ACID | pH 4 | pH 4 | pH 4 | pH 4 |
| | WATER | QS to 100 | QS to 100 | QS to 100 | QS to 100 |

Example 2

(Inventive Compositions with Silicone Oil)

| | INCI US | E | F | G | H |
|---|---|---|---|---|---|
| Glucosamine | GLUCOSAMINE HCl | 1 | 1 | 1 | 1 |
| Chitosan | CHITOSAN | 1 | 0.5 | 0.5 | 0.5 |
| Amino Silicone | AMODIMETHICONE | 1 | 2 | 5 | 7.5 |
| Nonionic | TRIDECETH-5 | 0.4 | 0.8 | 2 | 3 |
| Emulsifiers | TRIDECETH-10 | 0.1 | 0.2 | 0.5 | 0.8 |
| Water-Soluble Solvent | GLYCERIN | 0.2 | 0.5 | 1.2 | 1.8 |
| pH Adjuster | ACETIC ACID, LACTIC ACID | pH 4 | pH 4 | pH 4 | pH 4 |
| Preservative | PHENOXYETHANOL | 0.1 | 0.1 | 0.3 | 0.5 |
| | WATER | QS to 100 | QS to 100 | QS to 100 | QS to 100 |

Example 3

(Comparative Testing)

Comparative with Composition A (Coconut Oil)

| Composition | (HLB) | Comparative A-1 | Comparative A-2 | Inventive A |
|---|---|---|---|---|
| Glucosamine HCl | | — | — | 1 |
| Chitosan | | — | — | 1 |
| Lactic Acid | | to pH 4 | to pH 4 | to pH 4 |
| DI Water | | QS to 100 | QS to 100 | QS to 100 |
| Coconut Oil | 8 | — | 1 | 1 |
| Glyceryl stearate | 3.8 | — | 0.65 | 0.65 |
| Steareth 20 | 15.3 | — | 0.175 | 0.175 |
| Stearyl alcohol | 14 | — | 0.175 | 0.175 |
| Final HLB of composition | 7.6 | | | |

Comparative with Composition B (Olive Oil)

| Composition | (HLB) | Comparative B-1 | Comparative B-2 | Inventive B |
|---|---|---|---|---|
| Glucosamine HCl | | — | — | 1 |
| Chitosan | | — | — | 1 |
| Lactic Acid | | to pH 4 | to pH 4 | to pH 4 |
| DI Water | | QS to 100 | QS to 100 | QS to 100 |
| Olive Oil | 7 | — | 1 | 1 |
| Glyceryl stearate | 3.8 | — | 0.75 | 0.75 |
| Steareth 20 | 15.3 | — | 0.125 | 0.125 |
| Stearyl alcohol | 14 | — | 0.125 | 0.125 |
| Final HLB of composition | 6.5 | | | |

Comparative with Composition C (Palm Oil)

| Composition | (HLB) | Comparative C-1 | Comparative C-2 | Inventive C |
|---|---|---|---|---|
| Glucosamine HCl | | — | — | 1 |
| Chitosan | | — | — | 1 |
| Lactic Acid | | to pH 4 | to pH 4 | to pH 4 |
| DI Water | | QS to 100 | QS to 100 | QS to 100 |
| Palm Oil | 8 | — | 1 | 1 |
| Glyceryl stearate | 3.8 | — | 0.65 | 0.65 |
| Steareth 20 | 15.3 | — | 0.175 | 0.175 |
| Stearyl alcohol | 14 | — | 0.175 | 0.175 |
| Final HLB of composition | 7.6 | | | |

Comparative with Composition D (Soybean Oil)

| Composition | (HLB) | Comparative D-1 | Comparative D-2 | Inventive D |
|---|---|---|---|---|
| Glucosamine HCl | | — | — | 1 |
| Chitosan | | — | — | 1 |
| Lactic Acid | | to pH 4 | to pH 4 | to pH 4 |
| DI Water | | QS to 100 | QS to 100 | QS to 100 |
| Soybean Oil | 7 | — | 1 | 1 |
| Glyceryl stearate | 3.8 | — | 0.75 | 0.75 |
| Steareth 20 | 15.3 | — | 0.125 | 0.125 |
| Stearyl alcohol | 14 | — | 0.125 | 0.125 |
| Final HLB of composition | 6.5 | | | |

Treatment Protocol

Bleached hair swatches were treated according to the following treatment protocol.

The hair swatches were initially shampooed. After shampooing, excess water is removed using paper towels. About 0.4 grams of a composition per gram of hair is sprayed onto the damp hair swatches and the hair swatches are massaged using an applicator brush or comb and hands to ensure that the compositions penetrate the hair swatches. The hair swatches are then allowed to stand for about 5 minutes. After about 5 minutes, the hair swatches are dried using a blow dryer to about 80% dryness. The hair swatches are then completely dried using a blow dryer while simultaneously brushing the hair (about 20 brush passes). After complete drying, the hair is treated with 3 passes of a flat iron at a temperature of about 190° C. The hair is combed between each pass with the hot iron in order to align the hair fibers. The protocol is carried out once (1×) or repeated three times (3×).

Hair swatches treated according to the above protocol were subjected to thermal testing, cyclic fatigue testing, cuticle cohesion testing, dry friction testing, and wet friction testing. The testing and the results are discussed below.

Thermal Testing (DSC)

Differential Scanning Calorimetry ("DSC") is a tool for investigating the structural characteristics of hair fibers. Keratin undergoes detectable transformations at various temperatures. Changes in these transformation temperatures are used to illustrate how a particular hair-treatment influences hair fibers. Denaturation temperature ($T_d$) represents the thermal stability of hair fibers. Denaturation temperature and its relationship in determining the thermal stability of hair fibers is established in the literature. A higher $T_d$ value means that more heat is required to denature the keratin protein, indicating higher quality hair fibers.

DSC was used to measure the $T_d$ of untreated hair swatches (control), hair swatches treated 3× as described above with Inventive Composition B, and hair swatches treated 3× as described above with Comparative Composition B-2. All swatches were double bleached. DSC was conducted using a TA Instruments DSC 2500 with 4 pans prepared for each composition. The fibers were cut to a fine size, and about 8 mg was measured into each pan. About 50 µL of DI water was added to each pan and mixed with the fibers. The pans sat overnight before being heated from 40-180° C. at a rate of 10° C./min. The hair swatches treated with Inventive Composition B exhibited a significantly higher $T_d$ value compared to the untreated hair swatches and compared to the hair swatches treated with Comparative Composition B-2. The results are graphically presented in FIG. 1.

Cyclic Fatigue Testing

Figure 2:
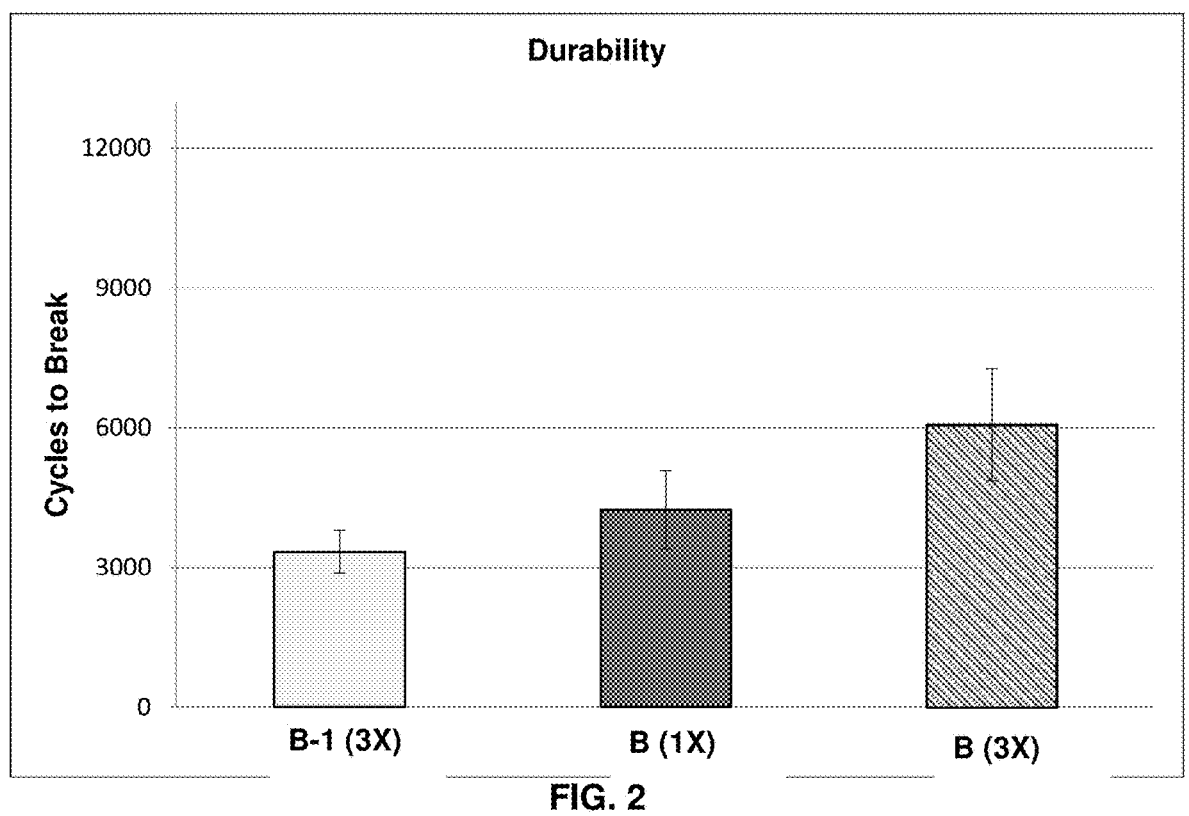
FIG. 2 graphically shows the Cyclic Fatigue Tensile Testing (CFTT) results for untreated hair, hair treated with a comparative composition, and hair treated with an inventive composition.

Cyclic Fatigue Tensile Testing (CFTT) is a method for determining the durability of fibers. Hair swatches were subjected to CFTT that were treated 3× with Comparative Composition B-1 (placebo), treated 1× with Inventive Composition B, or treated 3× with inventive Composition B. CFTT was conducted using a Dia-Stron CYC801 and FDAS 770. Forty fibers from each composition were crimped with 30 mm of fiber exposed between the crimps. The fibers were equilibrated overnight at 25° C. and relative humidity 45%. The cross section dimensional data was collected under these same conditions with measurements made along the fiber. The CFTT was run under constant stress mode (using plateau stress obtained using MTT), and Kaplan-Meier statistical analysis was performed using SPSS software. Hair swatches treated 1× with Inventive Composition B required more cycles to break than hair swatches treated 3× with Comparative Composition B-1 (placebo). Hair swatches treated 3× with Inventive Composition B required more cycles to break than hair swatches treated 1× with Inventive Composition B. This illustrates that treatment with Inventive Composition B improves the durability of the hair and that multiple treatments further improves durability of the hair. The results are graphically presented in FIG. 2.

Cuticle Cohesion Testing

Figure 3:
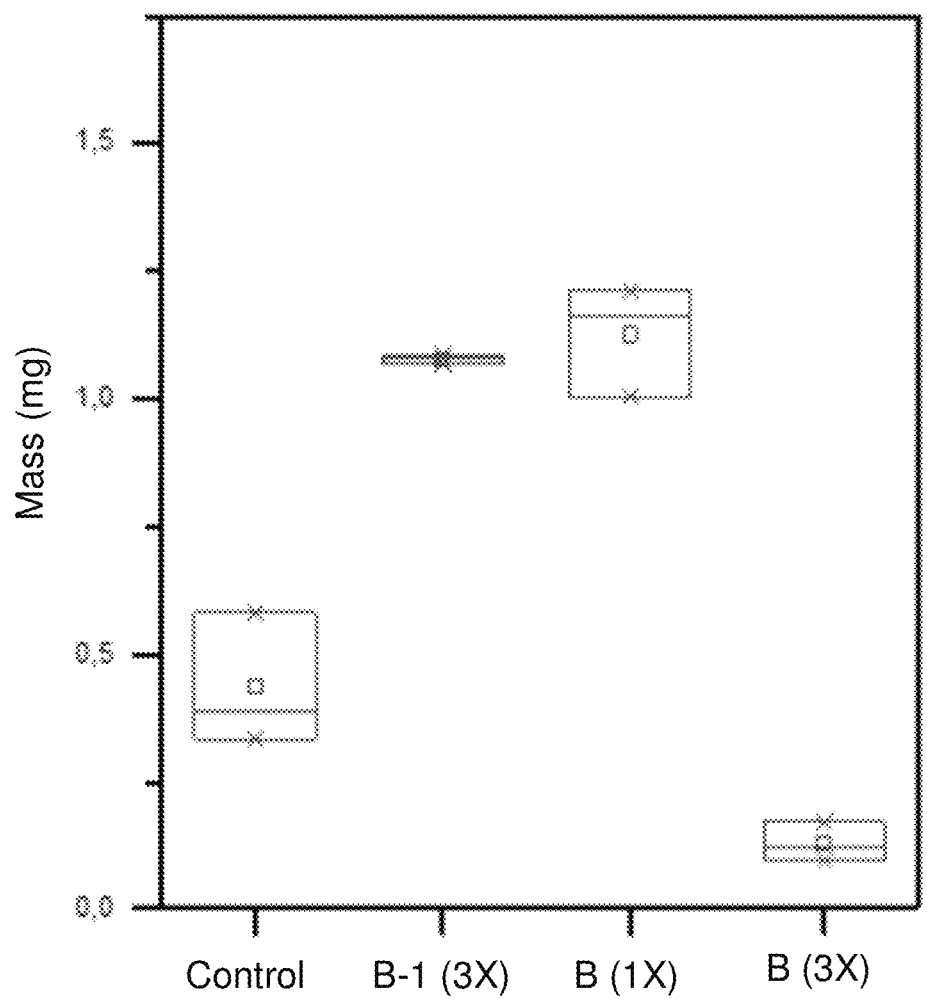
FIG. 3 graphically shows the cuticle cohesion testing results for untreated hair, hair treated with a comparative composition, and hair treated with an inventive composition.

Cuticle cohesion testing is used to quantify breakage of the cuticle from the hair fiber, and is used as an indication of hair damage. Higher cuticle cohesion illustrates less breakage (less cuticle is broken away from the hair fibers). Untreated hair swatches (control), hair swatches treated 3× with Comparative Composition B-1 (placebo), hair swatches treated 1× with Inventive Composition B, and hair swatches treated 3× with inventive Composition B were subjected to cuticle cohesion testing. All hair swatches were double bleached. The mass of the cuticle that separated from the fibers was determined. Cuticle cohesion testing was performed by cutting fibers to a size of about 6 mm, measuring out about 30 mg of hair and adding it to about 1.5 mL of water. The solution was centrifuged for about 19 minutes at a rate of 5000 RPM. The supernatant was removed, and additional liquid was evaporated. The remaining material was then measured. Hair swatches treated 3× with Inventive Composition B showed significantly higher cuticle cohesion (least amount of cuticle separation) than the other hair swatches tested. The results are graphically presented in FIG. 3.

Dry Friction Testing

Dry friction testing is used to measure the lubrication properties of hair fibers. A lower friction force represents better lubrication properties. Untreated hair swatches (control), hair swatches treated 3× with Comparative Composition B-1 (placebo), hair swatches treated 1× with Inventive Composition B, and hair swatches treated 3× with inventive Composition B were subjected to dry friction testing. All hair swatches were double bleached. Dry friction testing was performed by placing a bundle of fibers in between two rubber grips with a given normal force of 50 g at a temperature of 25° C. and 45% relative humidity. The bundle was pulled up at a constant speed of 100 mm/min, while the force (N) was measured as a function of displacement (mm), and an average friction force was calculated. The average friction forces (N) are reported in the table below.

|  | Bleached | B-1 (3×) | B (1×) | B (3×) |
| --- | --- | --- | --- | --- |
| Count | 4 | 4 | 4 | 4 |
| Median | 0.64 | 0.65 | 0.47 | 0.48 |
| Avg. | 0.63 | 0.66 | 0.47 | 0.47 |
| Std. Dev. | 0.04 | 0.01 | 0.02 | 0.03 |
| Outlier | 0 | 0 | 0 | 1 |

As shown in the table above, the dry friction force was significantly reduced for hair swatches treated 1× and 3× with Inventive Composition B, illustrating significantly better lubrication.

Wet Friction Testing

Wet friction testing is used to investigate the lubrication properties of hair fibers. A lower wet friction force represents better lubrication of the hair fibers. A higher wet friction force is associated with adhesiveness (stickiness) of the hair fibers to each other. Untreated hair swatches (control), hair swatches treated 3× with Comparative Composition B-1 (placebo), hair swatches treated 1× with Inventive Composition B, and hair swatches treated 3× with inventive Composition B were subjected to wet friction testing. All hair swatches were double bleached. Wet friction testing was performed by immersing a bundle of fibers in DI water for one minute before placing it in between two rubber grips with a given normal force of 50 g at a temperature of 25° C. and 45% relative humidity. The bundle was pulled up at a constant speed of 100 mm/min, while the force (N) was measured as a function of displacement (mm), and an average friction force was calculated. The average friction forces (N) are reported in the table below.

|  | Bleached | B-1 (3×) | B (1×) | B (3×) |
| --- | --- | --- | --- | --- |
| Count | 4 | 4 | 4 | 4 |
| Median | 0.56 | 0.94 | 0.47 | 0.45 |
| Avg. | 0.56 | 0.95 | 0.47 | 0.46 |
| Std. Dev. | 0.01 | 0.03 | 0.01 | 0.02 |
| Outlier | 0 | 1 | 1 | 0 |

As shown in the table above, the wet friction force was significantly reduced for hair swatches treated 1× and 3× with Inventive Composition B, illustrating significantly better lubrication.

Example 4

Heat Testing

Testing was carried out to determine the impact of heat on the adhesion and cohesion properties of films formed by compositions containing glucosamine and chitosan. An aqueous composition containing 1 wt. % of glucosamine HCL and 1 wt. % of chitosan ("GC Composition") was applied to one side of two glass slides. The glass slides were allowed to air dry so that a film would form on the slides. One of the glass slides was then heated to a temperature of 190° C. for 3 minutes in a preheated oven. The other glass slide was not subjected to heating. Both slides were then immersed into an aqueous cleansing solution containing 1 wt. % of a cleansing shampoo. The film on the slide that was not treated with heat disintegrated quickly, within 10 minutes of immersion into the aqueous cleansing solution. The film on the slide that was treated with heat, however, remained intact and attached to the slide.

Further testing was carried using Inventive Compositions D, B, and E. Inventive Compositions D, B, and E were applied to glass slides, allowed to dry, and were heated to a temperature of 190° C. for 3 minutes in a preheated oven. The inclusion of soy oil (Inventive Composition D), olive oil (Inventive Composition B), and amodimethicone (Inventive Composition E), improved adhesion of the films to the glass slides. The film formed by Inventive Composition A (including soy oil) remained intact for at least 24 hours but portions of the intact film became detached from the slide. Inventive Composition B (including olive oil) remained intact for at least 24 hours and did not show visible signs of detachment from the slide. Inventive Composition E (including amodimethicone) exhibited the strongest adhesion and cohesion properties. The film formed by Inventive Composition E remained intact for at least 24 hours, did not show signs of detachment from the glass slide, and resisted rubbing by fingers.

Example 5

Contact Angle Testing

Figure 4:
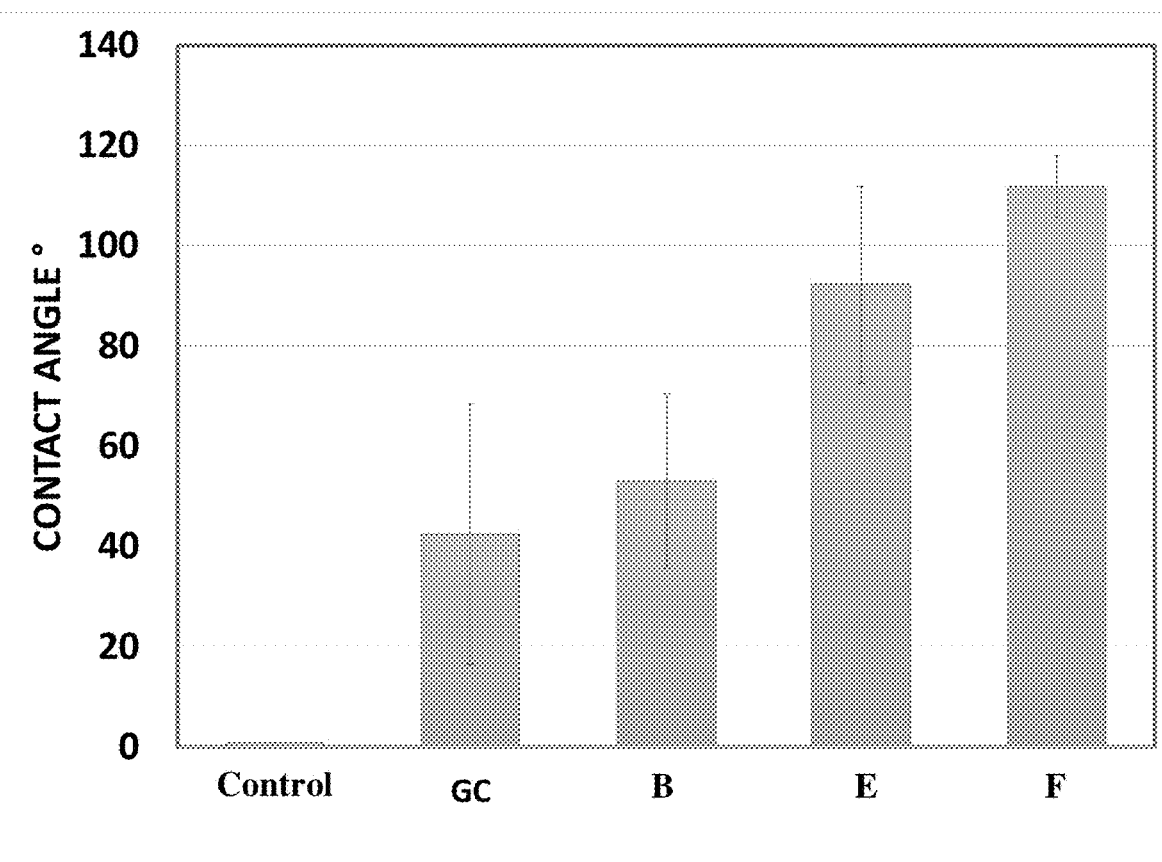
FIG. 4 graphically shows the contact angle of untreated hair, hair treated with glucosamine HCL and chitosan, and hair treated with inventive compositions.

Contact angle testing is used to quantify the hydrophobicity and the lastingness of the films applied to hair fibers. Testing was carried out on untreated hair swatches (control), hair swatches treated 3× with an aqueous composition containing 1 wt. % of glucosamine HCL and 1 wt. % of chitosan ("GC Composition"), and hair treated 3× with Inventive Compositions B (including olive oil), Inventive Composition E (including 1% amodimethicone), or Inventive Composition F (including 2% amodimethicone). All hair swatches were platinum bleached. The hair swatches were treated according to "Treatment Protocol" outlined above in Example 3. All of the hair swatches were then shampooed five times and subjected to contact angle testing. Contact angle measurements were performed using an Attension optical tensiometer in sessile drop mode. Three sections of each swatch were tested with 3 droplets per section (one toward root, one at mid, and one toward tip). The data show that treatment with glucosamine and chitosan significantly improve the hydrophobicity of the hair, even after being shampooed five times, which illustrates long lastingness. The addition of an oil in Inventive Compositions B, E, and F, further enhanced and increased hydrophobicity of the hair, even after being shampooed five times. Hair swatches treated with Inventive Composition F, which included the highest amount of oil (2% amodimethicone) provided the highest contact angle, indicating it provided the highest hydrophobicity to the hair swatches. The results are graphically presented in FIG. 4.

The foregoing description illustrates and describes the disclosure. Additionally, the disclosure shows and describes only the preferred embodiments but, as mentioned above, it is to be understood that it is capable to use in various other combinations, modifications, and environments and is capable of changes or modifications within the scope of the invention concepts as expressed herein, commensurate with the above teachings and/or the skill or knowledge of the relevant art. The embodiments described herein above are further intended to explain best modes known by applicant and to enable others skilled in the art to utilize the disclosure in such, or other, embodiments and with the various modifications required by the particular applications or uses thereof. Accordingly, the description is not intended to limit the invention to the form disclosed herein. Also, it is intended to the appended claims be construed to include alternative embodiments.

As used herein, the terms "comprising," "having," and "including" are used in their open, non-limiting sense.

The terms "a," "an," and "the" are understood to encompass the plural as well as the singular.

The expression "one or more" means "at least one" and thus includes individual components as well as mixtures/combinations.

Other than in the operating examples, or where otherwise indicated, all numbers expressing quantities of ingredients and/or reaction conditions are to be understood as being modified in all instances by the term "about," meaning within +/−5% of the indicated number.

All percentages, parts and ratios herein are based upon the total weight of the compositions of the present invention, unless otherwise indicated.

The term "treat" (and its grammatical variations) as used herein refers to the application of the hair-treatment compositions of the present disclosure onto the hair.

The term "monosaccharides" is understood to mean a monosaccharide sugar comprising at least 5 carbon atoms of formula $C_x(H_2O)_x$ with x an integer greater than or equal to 5, preferably x is greater than or equal to 6, in particular x is between 5 and 7 inclusive, preferably x=6, they may be of D or L configuration, and of alpha or beta anomer, and also the salts thereof and the solvates thereof such as hydrates.

The term "polysaccharides" is understood to mean a polysaccharide sugar which is a polymer constituted of several saccharides bonded to one another by O-glucosidic bonds, said polymers being constituted of monosaccharide units as defined previously, said monosaccharide units comprising at least 5 carbon atoms, preferably 6, particularly the monosaccharide units are connected to one another by 1,4 or 1,6 bond as α (alpha) or β (beta) anomer, it being possible for each saccharide unit to be of L or D configuration, and also the salts thereof and the solvates thereof such as the hydrates of said monosaccharides; more particularly they are polymers formed of a certain number of saccharides (or monosaccharides) having the general formula: $—[C_x(H_2O)_y)]_n$—where x is an integer greater than or equal to 5, preferably x is greater than or equal to 6, in particular x is between 5 and 7 inclusive and preferably x=6, and y is an integer which represents x−1, and n is an integer greater than or equal to 2, particularly of between 3 and 3000 inclusive, more particularly between 5 and 2500 and preferentially between 10 and 2300;

The term "with amine group(s)" is understood to mean that the monosaccharide(s) a) and the polysaccharide(s) are substituted with one or more $NR_1R_2$ amino group(s) i.e. at least one of the hydroxyl groups of at least one saccharide unit is replaced with an $NR_1R_2$ group with $R_1$ and $R_2$, which are identical or different, representing i) a hydrogen atom, ii) a (C1-C$_6$)alkyl group that is optionally substituted, preferably with one or more hydroxyl or $NH_2$ groups, iii) an aryl group such as phenyl, iv) an aryl($C_1$-$C_4$)alkyl group such as benzyl, v) a (hetero)cyclo($C_5$-$C_7$)alkyl group such as cyclohexyl, morpholinyl, piperazinyl, piperidinyl, vi) a (hetero)cyclo($C_5$-$C_7$)alkyl($C_1$-$C_4$)alkyl group such as cyclohexylmethyl, vii) —C(Y)—(Y')$_p$—R'$_1$ with Y and Y', which are identical or different, representing an oxygen atom, sulfur atom or N(R'$_2$), preferably oxygen, p=0 or 1, preferably 0; and R'$_1$ and R'$_2$ representing i) to vi) of $R_1$ and $R_2$ defined previously, and in particular R'$_1$ denoting a ($C_1$-$C_6$)alkyl group such as methyl. Preferably $R_1$ and $R_2$ represent a hydrogen atom or a ($C_1$-$C_4$)alkylcarbonyl group such as acetyl.

The term "low molecular weight" is understood to mean that the polysaccharide with amine group has an average molecular weight of less than 400 000 Da.

The term "organic or mineral acid salt" is more particularly understood to mean organic or mineral acid salts in particular chosen from a salt derived from i) hydrochloric acid HCl, ii) hydrobromic acid HBr, iii) sulfuric acid $H_2SO_4$, iv) alkylsulfonic acids: Alk-S(O)$_2$OH such as methylsulfonic acid and ethylsulfonic acid; v) arylsulfonic acids: Ar—S(O)$_2$OH such as benzenesulfonic acid and toluenesulfonic acid; vi) alkoxysulfinic acids: Alk-O—S(O)OH such as methoxysulfinic acid and ethoxysulfinic acid; vii) aryloxysulfinic acids such as tolueneoxysulfinic acid and phenoxysulfinic acid; viii) phosphoric acid $H_3PO_4$; ix) triflic acid $CF_3SO_3H$ and x) tetrafluoroboric acid $HBF_4$; xi) organic monocarboxylic acids (I) R—C(O)—OH with R representing a (hetero)aryl group such as phenyl, a (hetero)aryl($C_1$-$C_4$)alkyl such as benzyl, or ($C_1$-$C_{30}$)alkyl or an unsaturated $C_2$-$C_{30}$ radical (i.e. comprising at least one ethylenic unsaturation, preferably one ethylenic unsaturation) said alkyl group or unsaturated $C_2$-$C_{30}$ radical being optionally interrupted and/or optionally substituted preferably with one or more hydroxyl groups and not substituted with one or more amino radicals, R preferably denoting a ($C_1$-$C_6$)alkyl group optionally interrupted and/or optionally substituted with 1, 2 or 3 hydroxyl groups, preferably R represents a ($C_1$-$C_4$)alkyl group such as methyl or ethyl; in particular the organic monocarboxylic acids (I) are chosen from acetic acid, glycolic acid and lactic acid, more particularly from acetic acid and lactic acid, and xii) the polycarboxylic acids of formula (II) below:

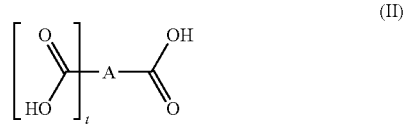

(II)

in which formula (II):

A represents a saturated or unsaturated, cyclic or noncyclic, aromatic or nonaromatic, polyvalent hydrocarbon-based group comprising from 1 to 30 carbon atoms optionally interrupted with one or more heteroatoms such as oxygen and/or optionally substituted in particular with one or more hydroxyl groups and t represents an integer between 1 and 5 inclusive; preferably A represents a divalent ($C_1$-$C_6$) alkylene group optionally substituted in particular with one or more hydroxyl groups and not substituted with at least one amino radical, and t is equal to 1, 2 or 3, the polycarboxylic acids of formula (II) are preferably chosen from tartaric acid, succinic acid, fumaric acid and citric acid and more particularly chosen from tartaric acid, succinic acid, fumaric acid, maleic acid and citric acid; and xiii) amino acids comprising more carboxylic acid radicals than amino groups such as gamma-carboxyglutamic acid, aspartic acid, glutamic acid, in particular gamma-carboxyglutamic acid; in particular the salts of monocarboxylic acids different from pyrrolidonecarboxylic acid, 100 OE and 500 OE ethoxylated stearic acid and linoleic acid, more particularly of monocarboxylic acid of formula.

An "alkyl radical" is a linear or branched $C_1$-$C_{10}$, preferably $C_1$-$C_6$ and in particular $C_1$-$C_4$ hydrocarbon-based radical, such as methyl or ethyl, unless otherwise indicated.

A ($C_x$-$C_y$)alkyl radical is a linear or branched $C_x$-$C_y$ hydrocarbon-based radical.

The expression "optionally interrupted" attributed to the alkyl radical or to the polyvalent group A defined previously is understood to mean that said radical may be interrupted with one or more groups or heteroatoms chosen from O, S, CO or combinations thereof such as —CO—O— or —O—CO—, preferably interrupted with one or more non-adjacent oxygen atoms.

The expression "optionally substituted" attributed to the alkyl radical or to the polyvalent group A defined previously is understood to mean that said radical may be substituted with one or more radicals chosen from the following radicals i) hydroxyl, ii) $C_1$-$C_4$ alkoxy, iii) acylamino, iv) amino optionally substituted with one or two identical or different $C_1$-$C_4$ alkyl radicals, said alkyl radicals possibly forming, with the nitrogen atom that bears them, a 5- to 7-membered heterocycle, optionally comprising another nitrogen or non-nitrogen heteroatom.

An "alkoxy radical" is an alkyl-oxy radical for which the alkyl radical is a linear or branched $C_1$-$C_{10}$, preferentially $C_1$-$C_6$ and more particularly $C_1$-$C_4$ hydrocarbon-based radical such as methoxy or ethoxy. When the alkoxy group is optionally substituted, this implies that the alkyl group is optionally substituted as defined hereinabove.

The "aryl" or "heteroaryl" radicals or the aryl or heteroaryl part of a radical may be substituted with at least one substituent borne by a carbon atom, chosen from one of the following atoms or groups:

halogen;
optionally substituted C1-$C_6$, preferably $C_1$-$C_4$, alkyl;
hydroxyl;
$C_1$-$C_2$ alkoxy;
$C_1$-$C_4$ (poly)hydroxyalkoxy;
amino;
5- or 6-membered heterocycloalkyl;
5- or 6-membered heteroaryl, optionally substituted with a ($C_1$-$C_4$)alkyl radical, preferentially methyl;
amino substituted with one or two optionally substituted, identical or different $C_1$-$C_6$ alkyl radicals:
acylamino (—NR—C(O)—R') in which the R radical is a hydrogen atom or a $C_1$-$C_4$ alkyl radical optionally bearing at least one hydroxyl group and the R' radical is a C1-$C_2$ alkyl radical;
carbamoyl ((R)$_2$N—C(O)—) in which the R radicals, which may be identical or different, represent a hydrogen atom or a $C_1$-$C_4$ alkyl radical optionally bearing at least one hydroxyl group;
alkylsulfonylamino (R'—S(O)$_2$—N(R)—) in which the R radical represents a hydrogen atom or a $C_1$-$C_4$ alkyl radical optionally bearing at least one hydroxyl group and the radical R' represents a $C_1$-$C_4$ alkyl radical, or a phenyl radical;

aminosulfonyl (($R)_2$N—S(O)$_2$—) in which the R radicals, which may be identical or different, represent a hydrogen atom or a $C_1$-$C_4$ alkyl radical optionally bearing at least one hydroxyl group;

cyano;

nitro or nitroso; and polyhaloalkyl, preferentially trifluoromethyl;

The cyclic or heterocyclic part of a non-aromatic group may be substituted with at least one substituent chosen from the following groups:

hydroxyl;

$C_1$-$C_4$ alkoxy or $C_2$-$C_4$ (poly)hydroxyalkoxy;

$C_1$-$C_4$ alkyl;

alkylcarbonylamino (R—C(O)—N(R')—), in which the R' radical is a hydrogen atom or a $C_1$-$C_4$ alkyl radical optionally bearing at least one hydroxyl group and the R radical is a $C_1$-$C_2$ alkyl group or an amino optionally substituted with one or two identical or different $C_1$-$C_4$ alkyl groups themselves optionally bearing at least one hydroxyl group;

alkylcarbonyloxy (R—C(O)—O—), in which the R radical is a $C_1$-$C_4$ alkyl radical or an amino group optionally substituted with one or two identical or different $C_1$-$C_4$ alkyl groups themselves optionally bearing at least one hydroxyl group;

alkoxycarbonyl (R-G-C(O)—), in which the R radical is a $C_1$-$C_4$ alkoxy radical and G is an oxygen atom, or an amino group optionally substituted with a $C_1$-$C_4$ alkyl group itself optionally bearing at least one hydroxyl group.

A cyclic or heterocyclic radical, or a non-aromatic part of an aryl or heteroaryl radical, may also be substituted with one or more oxo groups.

An "aryl" radical represents a monocyclic or fused or non-fused polycyclic carbon-based group, comprising from 6 to 22 carbon atoms, at least one ring of which is aromatic; such as phenyl, biphenyl, naphthyl, indenyl, anthracenyl or tetrahydronaphthyl, preferentially phenyl.

A "heteroaryl radical" represents an optionally cationic, 5- to 22-membered, monocyclic or fused or non-fused polycyclic group, comprising from 1 to 6 heteroatoms chosen from nitrogen, oxygen, sulfur and selenium atoms, at least one ring of which is aromatic; preferentially, a heteroaryl radical is chosen from acridinyl, (benz)imidazolyl, (benzo)bistriazolyl, (benzo)pyrazolyl, (benzo)pyridazinyl, (benzo)quinolyl, (benzo)thiazolyl, (benzo)triazolyl, (benz)oxazolyl, pyridyl, tetrazolyl, dihydrothiazolyl, imidazopyridyl, indolyl, isoquinolyl, naphthoimidazolyl, naphthoxazolyl, naphthopyrazolyl, oxadiazolyl, oxazolyl, oxazolopyridyl, phenazinyl, phenoxazolyl, pyrilyl, pyrazoyltriazyl, pyridyl, pyridinoimidazolyl, pyrrolyl, quinolyl, tetrazolyl, thiadiazolyl, thiazolopyridyl, thiazoylimidazolyl, thiopyrylyl, triazolyl and xanthyl.

A "heterocyclic radical" is a 5- to 22-membered monocyclic or fused or non-fused polycyclic radical comprising one or two unsaturations but is non-aromatic, comprising from 1 to 6 heteroatoms chosen from nitrogen, oxygen, sulfur and selenium atoms.

A "heterocycloalkyl radical" is a heterocyclic radical comprising at least one saturated ring.

A "limp" keratin fibres or "limp" hair is understood to mean that said fibres or hair are elastic, have no body, do not hold shape, the head of hair is flat without volume.

The expression "inclusive" for a range of concentrations means that the limits of the range are included in the defined interval.

"Conditioning" as used herein means imparting to one or more hair fibers at least one property chosen from combability, moisture-retentivity, luster, shine, and softness.

The state of conditioning can be evaluated by any means known in the art, such as, for example, measuring, and comparing, the ease of combability of the treated hair and of the untreated hair in terms of combing work (gm-in), and consumer perception.

The term "stable" as used herein means that the composition does not exhibit phase separation and/or crystallization.

"Volatile", as used herein, means having a flash point of less than about 100° C.

"Non-volatile", as used herein, means having a flash point of greater than about 100° C.

The salts referred to throughout the disclosure may include salts having a counter-ion such as an alkali metal, alkaline earth metal, or ammonium counter-ion. This list of counter-ions, however, is non-limiting.

Throughout the disclosure, the term "a mixture thereof" is used, following a list of elements as shown in the following example where letters A-F represent the elements: "one or more elements selected from the group consisting of A, B, C, D, E, F, and a mixture thereof." The term, "a mixture thereof" does not require that the mixture include all of A, B, C, D, E, and F (although all of A, B, C, D, E, and F may be included). Rather, it indicates that a mixture of any two or more of A, B, C, D, E, and F can be included. In other words, it is equivalent to the phrase "one or more elements selected from the group consisting of A, B, C, D, E, F, and a mixture of any two or more of A, B, C, D, E, and F."

Likewise, the term "a salt thereof" also relates to "salts thereof." Thus, where the disclosure refers to "an element selected from the group consisting of A, B, C, D, E, F, a salt thereof, and a mixture thereof," it indicates that that one or more of A, B, C, D, and F may be included, one or more of a salt of A, a salt of B, a salt of C, a salt of D, a salt of E, and a salt of F may be included, or a mixture of any two of A, B, C, D, E, F, a salt of A, a salt of B, a salt of C, a salt of D, a salt of E, and a salt of F may be included.

The expression "one or more" means "at least one" and thus includes individual components as well as mixtures/combinations.

All ranges and values disclosed herein are inclusive and combinable. For examples, any value or point described herein that falls within a range described herein can serve as a minimum or maximum value to derive a sub-range, etc. Furthermore, all ranges provided are meant to include every specific range within, and combination of sub ranges between, the given ranges. Thus, a range from 1-5, includes specifically 1, 2, 3, 4 and 5, as well as sub ranges such as 2-5, 3-5, 2-3, 2-4, 1-4, etc.

Other than in the operating examples, or where otherwise indicated, all numbers expressing quantities of ingredients and/or reaction conditions are to be understood as being modified in all instances by the term "about," meaning within +/−5% of the indicated number.

The term "substantially free" or "essentially free" as used herein means that there is less than about 2% by weight of a specific material added to a composition, based on the total weight of the compositions. Nonetheless, the compositions may include less than about 1 wt. %, less than about 0.5 wt. %, less than about 0.1 wt. %, or none of the specified material.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

The invention claimed is:

1. A hair-treatment composition in the form of an oil-in-water emulsion comprising:
   (a) about 0.5 to about 3 wt. % of glucosamine and/or a salt thereof;
   (b) about 0.5 to about 3 wt. % of chitosan;
      wherein (a) and (b) are solubilized in an aqueous phase of the oil-in-water emulsion;
   (c) about 0.5 to about 10 wt. % of one or more oils;
      wherein the composition is free from silicone oils;
   (d) about 0.5 to about 5 wt. % of one or more nonionic emulsifiers; and
   (e) water;
      wherein all weight percentages are based on the total weight of the composition;
      the composition has a pH of about 2 to about 6;
      the composition is not a shampoo; and
      the composition is free of succinic acid, gluconic acid, derivatives thereof, salts thereof, and a mixture thereof.

2. The composition of claim 1, wherein the weight ratio of (a) to (b) is 1:3 to about 3:1.

3. The composition of claim 1, wherein the pH is about 2 to about 5.

4. The composition of claim 1, wherein the one or more oils are natural oils.

5. The composition of claim 4, wherein the natural oils are vegetable oils selected from palm oil, soybean oil, olive oil, coconut oil, and a mixture thereof.

6. The composition of claim 4 comprising:
   one or more nonionic emulsifiers having an HLB of 10 or higher; and
   one or more nonionic emulsifiers having an HLB of 5 or less.

7. The composition of claim 1 comprising:
   (a) about 0.5 to about 3 wt. % of glucosamine and/or a salt thereof;
   (b) about 0.5 to about 3 wt. % of chitosan;
      wherein (a) and (b) are solubilized in an aqueous phase of the oil-in-water emulsion; and the weight ratio of (a) to (b) is about 3:1 to about 1:3;
   (c) about 0.5 10 wt. % of one or more natural oils;
   (d) about 0.5 to about 5 wt. % of two or more nonionic emulsifiers, wherein the two or more nonionic emulsifiers comprise:
      one or more nonionic emulsifiers having an HLB of 10 or higher; and
      one or more nonionic emulsifiers having an HLB of 5 or less; and
   (e) about 75 to about 98 wt. % of water;
      wherein all weight percentages are based on the total weight of the composition; and
      the composition has a pH of about 2 to about 6.

8. A method for treating hair comprising:
   (i) applying the hair-treatment composition of claim 1 to the hair;
   (ii) drying the hair;
   (iii) after applying the hair-treatment composition to the hair and drying the hair, heating the hair to a temperature above room temperature.

9. The method of claim 8 wherein the hair is heated using a hot iron.

10. A hair-treatment composition in the form of an oil-in-water emulsion comprising:
    (a) about 0.5 to about 2 wt. % of glucosamine and/or a salt thereof;
    (b) about 0.5 to about 2 wt. % of chitosan;
       wherein (a) and (b) are solubilized in an aqueous phase of the oil-in-water emulsion; and the weight ratio of (a) to (b) is about 2:1 to about 1:2;
    (c) about 0.1 to about 10 wt. % of one or more oils;
       wherein the composition is free from silicone oils;
    (d) about 0.5 to about 3 wt. % of two or more nonionic emulsifiers, wherein the two or more nonionic emulsifiers comprise:
       one or more nonionic emulsifier having an HLB of 10 or higher; and
       one or more nonionic emulsifiers having an HLB of 5 or less; and
    (e) about 75 98 wt. % of water;
       wherein all weight percentages are based on the total weight of the composition;
       the composition has a pH of about 2 to about 5.

11. The composition of claim 10, wherein the one or more oils are selected from natural oils.

12. The composition of claim 11, wherein the one or more natural oils are selected from are vegetable oils.

13. The composition of claim 12, wherein the vegetable oils are selected from palm oil, soybean oil, olive oil, coconut oil, or a mixture thereof.

14. The composition of claim 11, wherein the composition has a final HLB of within +/−0.5 of the HLB of the one or more natural oils.

15. The composition of claim 7, wherein the composition has a pH of about 2 to about 5.

16. The composition of claim 15, wherein the composition has a final HLB of within +/−0.5 of the HLB of the one or more natural oils.

* * * * *